United States Patent
Jacobine et al.

(10) Patent No.: US 8,106,141 B2
(45) Date of Patent: Jan. 31, 2012

(54) CURE ACCELERATORS FOR ANAEROBIC CURABLE COMPOSITIONS

(75) Inventors: Anthony F. Jacobine, Meriden, CT (US); Andrew Messana, Newington, CT (US); David M. Glaser, New Britain, CT (US); Steven Thomas Nakos, Andover, CT (US)

(73) Assignee: Henkel Corporation, Rocky Hill, CT (US)

(*) Notice: Subject to any disclaimer, the term of this patent is extended or adjusted under 35 U.S.C. 154(b) by 587 days.

(21) Appl. No.: 12/116,572

(22) Filed: May 7, 2008

(65) Prior Publication Data

US 2009/0277356 A1    Nov. 12, 2009

(51) Int. Cl.
*C08G 18/32* (2006.01)
*C08G 18/38* (2006.01)
*C08L 75/04* (2006.01)
*C09J 175/04* (2006.01)
*C07C 243/12* (2006.01)
*C07C 243/22* (2006.01)
*C07C 271/08* (2006.01)
*C07C 271/24* (2006.01)
*C07C 275/04* (2006.01)
*C07C 275/26* (2006.01)

(52) U.S. Cl. ............ 528/68; 252/182.17; 252/182.18; 524/717; 524/722; 524/723; 524/728; 525/123; 525/127; 525/128; 525/131; 525/452; 525/453; 525/454; 525/455; 528/44; 528/49; 528/69; 528/73; 528/74; 528/75; 528/85; 558/232; 558/234; 558/236; 558/237; 558/238; 558/239; 558/240; 558/242; 560/24; 560/25; 560/115; 560/157; 560/158; 564/32; 564/34; 564/44; 564/45

(58) Field of Classification Search ............ 528/69, 528/68, 73, 74, 75, 85, 44, 49; 558/232, 558/234, 236, 237, 238, 239, 240, 242; 524/717, 524/722, 723, 728; 525/123, 127, 128, 131, 525/452, 453, 454, 455

See application file for complete search history.

(56) References Cited

U.S. PATENT DOCUMENTS 3,218,305 A    11/1965 Krieble
(Continued)

FOREIGN PATENT DOCUMENTS

DE    1817989    12/1976
(Continued)

OTHER PUBLICATIONS

R.D. Rich, "Anaerobic Adhesives", Handbook of Adhesive Technology, Chapter 39, pp. 761-774 (2003).

(Continued)

*Primary Examiner* — Rabon Sergent
(74) *Attorney, Agent, or Firm* — Steven C. Bauman

(57) ABSTRACT

Reaction products prepared from reactants including: (a) at least one compound of structural Formula (I):

Formula (I)

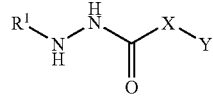

wherein $R^1$ is selected from aryl and heteroaryl; X is selected from a direct bond, —O—, —S—, —NH—, alkylene, cycloalkylene, heterocyclylene, arylene, alkarylene, and heteroarylene; Y is a substituted alkylene group having at least two contiguous carbon atoms and which can be interrupted by one or more —O—, —S—, or —NH— moieties as defined herein, wherein the alkylene group of Y has substituents independently selected from —OH, —NH$_2$, —SH, cycloalkyl, heterocyclyl, aryl, and heteroaryl, or two hydrogen atoms on the same carbon atom of Y are replaced by carbonyl, and wherein at least two substituents of Y are each independently selected from —OH, —NH$_2$, and —SH, as defined herein; and (b) at least one isocyanate functional material.

28 Claims, 3 Drawing Sheets

U.S. PATENT DOCUMENTS

| | | | |
|---|---|---|---|
| 3,970,505 A | 7/1976 | Hauser et al. | |
| 4,180,640 A | 12/1979 | Melody et al. | |
| 4,287,330 A | 9/1981 | Rich | |
| 4,321,349 A | 3/1982 | Rich | |
| 5,411,988 A | 5/1995 | Bockow et al. | |
| 5,496,695 A * | 3/1996 | Simpson et al. | 430/619 |
| 5,605,999 A | 2/1997 | Chu et al. | |
| 5,637,449 A * | 6/1997 | Harring et al. | 430/619 |
| 5,811,473 A | 9/1998 | Ramos et al. | |
| 6,391,993 B1 | 5/2002 | Attarwala et al. | |
| 6,583,289 B1 | 6/2003 | McArdle et al. | |
| 6,596,808 B1 * | 7/2003 | Newberth et al. | 524/812 |
| 6,676,795 B1 * | 1/2004 | Levandoski | 156/272.2 |
| 6,835,762 B1 | 12/2004 | Kelmarczyk et al. | |
| 6,897,277 B1 | 5/2005 | Kelmarczyk et al. | |
| 6,958,368 B1 | 10/2005 | Kelmarczyk et al. | |
| 7,115,676 B2 * | 10/2006 | Woods et al. | 523/176 |
| 2009/0278084 A1 * | 11/2009 | Messana et al. | 252/182.17 |
| 2009/0281335 A1 * | 11/2009 | Messana et al. | 549/449 |

FOREIGN PATENT DOCUMENTS

| | | |
|---|---|---|
| DE | 2806701 | 2/1978 |
| FR | 1581361 | 9/1969 |
| JP | 07-3008757 B | 12/1973 |

OTHER PUBLICATIONS

D.M. Young et al., "Polyesters from Lactones," Union Carbide F-40, p. 147.

* cited by examiner

CURE ACCELERATORS FOR ANAEROBIC CURABLE COMPOSITIONS

BACKGROUND OF THE INVENTION

1. Field of the Invention

The present invention relates to novel cure accelerators that can be useful for anaerobic curable compositions, such as adhesives and sealants.

2. Brief Description of Related Technology

Anaerobic adhesive compositions generally are well-known. See e.g. R. D. Rich, "Anaerobic Adhesives" in *Handbook of Adhesive Technology*, 29, 467-79, A. Pizzi and K. L. Mittal, eds., Marcel Dekker, Inc., New York (1994), and references cited therein. Their uses are legion and new applications continue to be developed.

Conventional anaerobic adhesives ordinarily include a free-radically polymerizable acrylate ester monomer, together with a peroxy initiator and an inhibitor component. Often, such anaerobic adhesive compositions also contain accelerator components to increase the speed with which the composition cures.

Desirable anaerobic cure-inducing compositions to induce and accelerate cure may include one or more of saccharin, toluidines, such as N,N-diethyl-p-toluidine ("DE-p-T") and N,N-dimethyl-o-toluidine ("DM-o-T"), acetyl phenylhydrazine ("APH"), maleic acid, and quinones, such as napthaquinone and anthraquinone. See e.g., U.S. Pat. No. 3,218,305 (Krieble), U.S. Pat. No. 4,180,640 (Melody), U.S. Pat. No. 4,287,330 (Rich) and U.S. Pat. No. 4,321,349 (Rich).

Saccharin and APH are used as standard cure accelerator components in anaerobic adhesive cure systems. The LOCTITE-brand anaerobic adhesive products currently available from Henkel Corporation use either saccharin alone or both saccharin and APH in most of its anaerobic adhesives. These components however have come under regulatory scrutiny in certain parts of the world, and thus efforts have been undertaken to identify candidates as replacements.

Examples of other curatives for anaerobic adhesives include thiocaprolactam (e.g., U.S. Pat. No. 5,411,988) and thioureas [e.g., U.S. Pat. No. 3,970,505(Hauser) (tetramethyl thiourea), German Patent Document Nos. DE 1 817 989 (alkyl thioureas and N,N'-dicyclohexyl thiourea) and 2 806 701 (ethylene thiourea), and Japanese Patent Document No. JP 07-3,008,757 (acyl, alkyl, alkylidene, alkylene and alkyl thioureas)], certain of the latter of which had been used commercially up until about twenty years ago.

Loctite (R&D) Ltd. discovered a new class of materials—trithiadiaza pentalenes—effective as curatives for anaerobic adhesive compositions. The addition of these materials into anaerobic adhesives as a replacement for conventional curatives (such as APH) surprisingly provides at least comparable cure speeds and physical properties for the reaction products formed therefrom. See U.S. Pat. No. 6,583,289 (McArdle).

U.S. Pat. No. 6,835,762 (Klemarczyk) provides an anaerobic curable composition based on a (meth)acrylate component with an anaerobic cure-inducing composition substantially free of acetyl phenylhydrazine and maleic acid and an anaerobic cure accelerator compound having the linkage —C(=O)—NH—NH— and an organic acid group on the same molecule, provided the anaerobic cure accelerator compound excludes 1-(2-carboxyacryloyl)-2-phenylhydrazine. The anaerobic cure accelerator is embraced by:

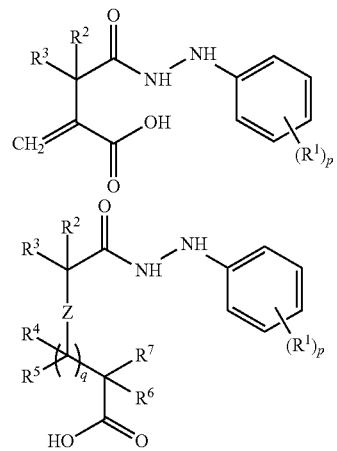

where $R^1$-$R^7$ are each independently selected from hydrogen and $C_{1-4}$; Z is a carbon-carbon single bond or carbon-carbon double bond; q is 0 or 1; and p is an integer between 1 and 5, examples of which are 3-carboxyacryloyl phenylhydrazine, methyl-3-carboxyacryloyl phenylhydrazine, 3-carboxypropanoyl phenylhydrazine, and methylene-3-carboxypropanoyl phenylhydrazine.

U.S. Pat. No. 6,897,277 (Klemarczyk) provides an anaerobic curable composition based on a (meth)acrylate component with an anaerobic cure-inducing composition substantially free of saccharin and an anaerobic cure accelerator compound within the following structure

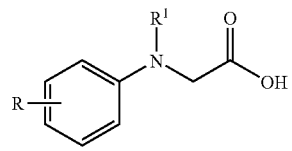

where R is selected from hydrogen, halogen, alkyl, alkenyl, hydroxyalkyl, hydroxyalkenyl, carboxyl, and sulfonato, and $R^1$ is selected from hydrogen, alkyl, alkenyl, hydroxyalkyl, hydroxyalkenyl, and aralkyl, an example of which is phenyl glycine and N-methyl phenyl glycine.

U.S. Pat. No. 6,958,368 (Messana) provides an anaerobic curable composition. This composition is based on a (meth) acrylate component with an anaerobic cure-inducing composition substantially free of saccharin and within the following structure

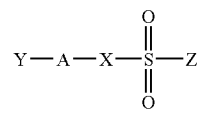

where Y is an aromatic ring, optionally substituted at up to five positions by $C_{1-6}$ alkyl or alkoxy, or halo groups; A is C=O, S=O or O=S=O; X is NH, O or S and Z is an aromatic ring, optionally substituted at up to five positions by $C_{1-6}$ alkyl or alkoxy, or halo groups, or Y and Z taken together may join to the same aromatic ring or aromatic ring system, provided that when X is NH, o-benzoic sulfimide is excluded from the structure. Examples of the anaerobic cure accelerator compound embraced by the structure above include 2-sulfobenzoic acid cyclic anhydride, and 3H-1,2-benzodithiol-3-one-1,1-dioxide.

Notwithstanding the state of the art, there is an on-going desire to find alternative technologies for anaerobic cure accelerators to differentiate existing products and provide supply assurances in the event of shortages or cessation of supply of raw materials. Moreover, since certain of the raw materials used in the anaerobic cure inducing composition have to one degree or another come under regulatory scrutiny, alternative components would be desirable. Accordingly, it would be desirable to identify new materials that function as cure components in the cure of anaerobically curable compositions.

SUMMARY OF THE INVENTION

In some non-limiting embodiments, the present invention provides reaction products prepared from reactants comprising: (a) at least one compound selected from the group of compounds represented by structural Formula (I):

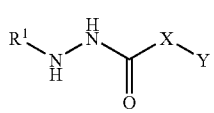

Formula (I)

wherein in Formula I: $R^1$ is selected from the group consisting of aryl and heteroaryl; X is selected from the group consisting of a direct bond, —O—, —S—, —NH—, alkylene, cycloalkylene, heterocyclylene, arylene, alkarylene, and heteroarylene; Y is a substituted alkylene group comprising an alkylene backbone having at least two contiguous carbon atoms and which optionally can be interrupted by one or more —O—, —S—, or —NH— moieties, provided that each —O—, —S—, or —NH— moiety of Y, if present, is not adjacent to an —O—, —S—, or —NH— of X, wherein the alkylene group of Y has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl, and wherein at least two substituents of Y are each independently selected from the group consisting of —OH, —NH$_2$, and —SH, and provided that each of the —OH, —NH, -or —SH groups is not attached to the same carbon atom of Y or an —O—, —S—, or —NH— backbone moiety of Y; and (b) at least one isocyanate functional material.

In some non-limiting embodiments, the present invention provides reaction products prepared from reactants comprising: (a) at least one reaction product (A) prepared from reactants comprising: (1) at least one compound selected from the group of compounds represented by structural Formula (II):

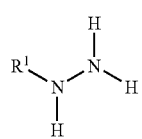

Formula (II)

wherein in Formula II: $R^1$ is selected from the group consisting of aryl and heteroaryl; and (2) at least one compound selected from the group of compounds represented by structural Formula (III) and structural Formula (IV):

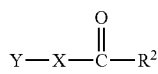

Formula (III)

wherein in Formula III: X is selected from the group consisting of a direct bond, —O—, —S—, —NH—, alkylene, cycloalkylene, heterocyclylene, arylene, alkarylene, and heteroarylene; Y is a substituted alkylene group comprising an alkylene backbone having at least two contiguous carbon atoms and which optionally can be interrupted by one or more —O—, —S—, or —NH— moieties, provided that each —O—, —S—, or —NH— moiety of Y, if present, is not adjacent to an —O—, —S—, or —NH— of X, wherein the alkylene group of Y has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl, and wherein at least two substituents of Y are each independently selected from the group consisting of —OH, —NH$_2$, and —SH, and provided that each of the —OH, —NH, -or —SH groups is not attached to the same carbon atom of Y or an —O—, —S—, or —NH— backbone moiety of Y; and $R^2$ is selected from the group consisting of —OR, NHR, alkyl, and arylalkyl, wherein R is H, alkyl or arylalkyl; and

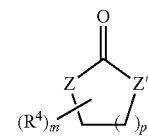

Formula (IV)

wherein in Formula IV: Z and Z' are each independently selected from the group consisting of —O—, —S—, and —NR$^3$, wherein $R^3$ is H or alkyl; m is at least 1; each $R^4$ is independently selected from the group consisting of hydroxyalkyl, aminoalkyl, thioalkyl, hydroxyl substituted cycloalkyl, arylalkyl having at least one —OH, —NH$_2$, or —SH group, and heteroarylalkyl having at least one —OH, —NH$_2$, or —SH group, provided that there is no more than one $R^4$ substituent attached to a substitutable ring carbon atom; and p is 1 or 2; and (b) at least one isocyanate functional material.

In some non-limiting embodiments, the present invention provides reaction products prepared from reactants comprising: (a) at least one reaction product (B) prepared from reactants comprising: (1) at least one compound selected from the group of compounds represented by structural Formula (V):

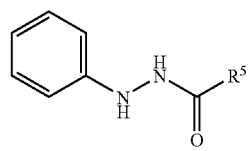

Formula (V)

wherein in Formula V: $R^5$ is selected from the group consisting of hydroxyalkyl and carboxyalkyl; and (2) at least one compound selected from the group of compounds represented by structural Formula (VI):

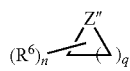

Formula (VI)

wherein in Formula VI: Z" is selected from the group consisting of —O—, —S—, and —NH—; q is 1 to 4; $R^6$ is independently selected from the group consisting of hydroxyalkyl, aminoalkyl, and thioalkyl; and n is at least 1; and (b) at least one isocyanate functional material.

In some non-limiting embodiments, the present invention provides methods of making a reaction product prepared from reactants comprising reacting: (a) at least one compound selected from the group of compounds represented by structural Formula (I):

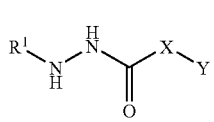

Formula (I)

wherein in Formula I: $R^1$ is selected from the group consisting of aryl and heteroaryl; X is selected from the group consisting of a direct bond, —O—, —S—, —NH—, alkylene, cycloalkylene, heterocyclylene, arylene, alkarylene, and heteroarylene; Y is a substituted alkylene group comprising an alkylene backbone having at least two contiguous carbon atoms which optionally can be interrupted by an —O—, —S—, or —NH— moiety, provided that the —O—, —S—, or —NH— of Y, if present, is not adjacent to another —O—, —S—, or —NH— group of X, wherein the alkylene group has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl, and wherein at least two substituents are each independently selected from the group consisting of —OH, —NH$_2$, and —SH, and provided that each of the —OH, —NH, -or —SH is not attached to the same carbon atom of Y or an —O—, —S—, or —NH— backbone moiety of Y; and (b) at least one isocyanate functional material.

BRIEF DESCRIPTION OF THE FIGURES

The foregoing summary, as well as the following detailed description, will be better understood when read in conjunction with the appended drawings. In the drawings.

DETAILED DESCRIPTION OF THE INVENTION

Figure 1:
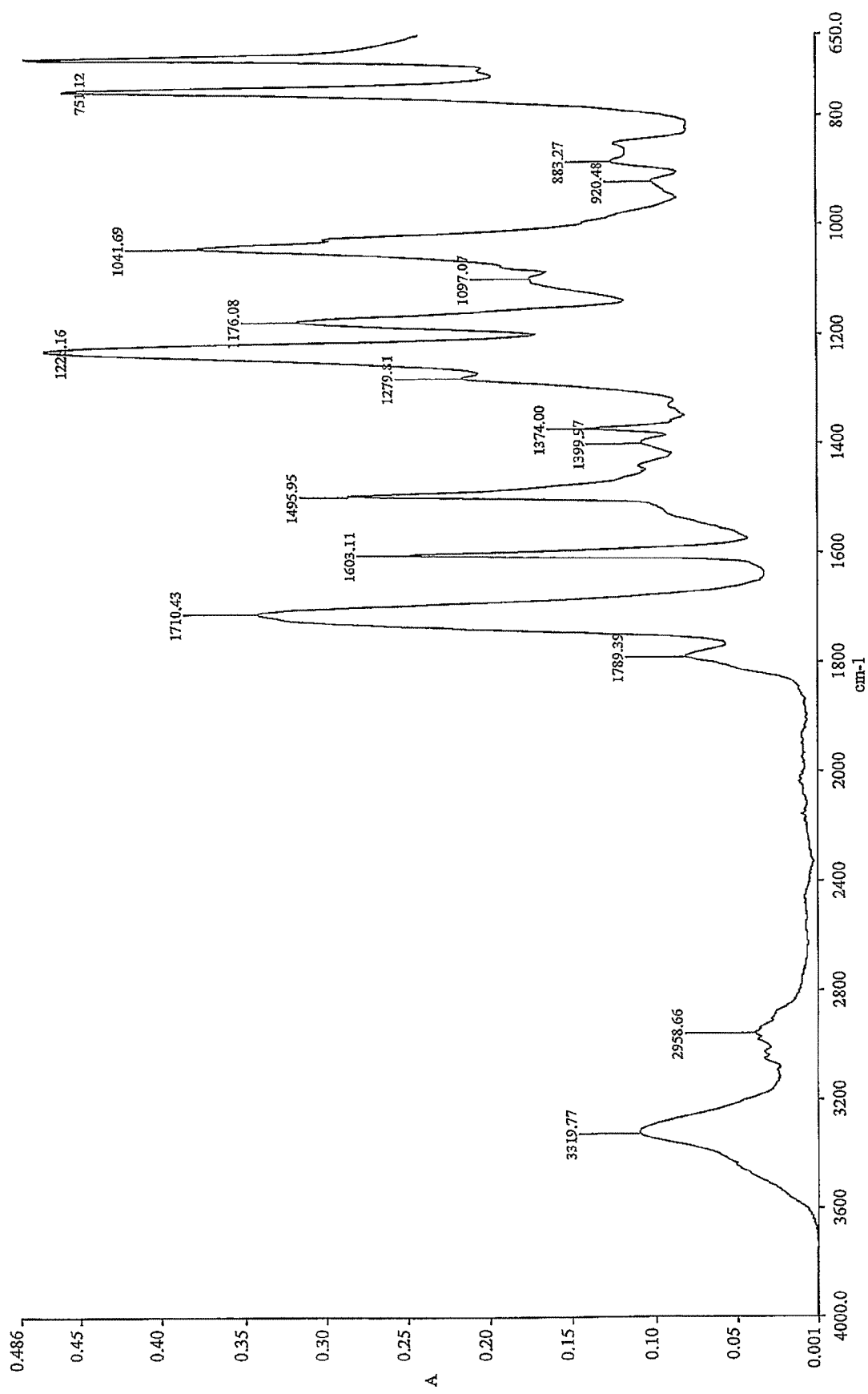
FIG. 1 depicts an IR spectra of a phenylhydrazine-glycerol carbonate reaction product of Example A according to the present invention.

Other than in the operating examples, or where otherwise indicated, all numbers expressing quantities of ingredients, thermal conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

As used herein, the term "composition" is intended to encompass a product comprising the specified ingredients in the specified amounts, as well as any product which results, directly or indirectly, from combination of the specified ingredients in the specified amounts.

As used herein, "formed from" or "prepared from" denotes open, e.g., "comprising," claim language. As such, it is intended that a composition "formed from" or "prepared from" a list of recited components be a composition comprising at least these recited components or the reaction product of at least these recited components, and can further comprise other, non-recited components, during the composition's formation or preparation.

As used herein, the phrase "reaction product of" means chemical reaction product(s) of the recited components, and can include partial reaction products as well as fully reacted products.

As used herein, the term "polymer" in meant to encompass oligomers, and includes without limitation both homopolymers and copolymers. The term "prepolymer" means a compound, monomer or oligomer used to prepare a polymer, and includes without limitation both homopolymer and copolymer oligomers. The term "oligomer" means a polymer consisting of only a few monomer units up to about ten monomer units, for example a dimer, trimer or tetramer.

As used herein, the term "cure" as used in connection with a composition, e.g., "composition when cured" or a "cured composition", means that any curable or crosslinkable components of the composition are at least partially cured or crosslinked. In some non-limiting embodiments of the present invention, the chemical conversion of the crosslinkable components, i.e., the degree of crosslinking, ranges from about 5% to about 100% of complete crosslinking where complete crosslinking means full reaction of all crosslinkable components. In other non-limiting embodiments, the degree of crosslinking ranges from about 15% to about 80% or about 50% to about 60% of full crosslinking. One skilled in the art will understand that the presence and degree of crosslinking, i.e., the crosslink density, can be determined by a variety of methods, such as dynamic mechanical thermal analysis (DMA) using a TA Instruments DMA 2980 DMA analyzer over a temperature range of −65° F. (−18° C.) to 350° F. (177° C.) conducted under nitrogen according to ASTM D 4065-01. This method determines the glass transition temperature and crosslink density of free films of coatings or polymers. These physical properties of a cured material are related to the structure of the crosslinked network.

Curing of a polymerizable composition can be obtained by subjecting the composition to curing conditions, such as but not limited to heating, etc., leading to the reaction of reactive groups of the composition and resulting in polymerization and formation of a solid polymerizate. When a polymerizable composition is subjected to curing conditions, following polymerization and after reaction of most of the reactive groups occurs, the rate of reaction of the remaining unreacted reactive groups becomes progressively slower. In some non-limiting embodiments, the polymerizable composition can be subjected to curing conditions until it is at least partially cured. The term "at least partially cured" means subjecting the polymerizable composition to curing conditions, wherein reaction of at least a portion of the reactive groups of the composition occurs, to form a solid polymerizate. In some non-limiting embodiments, the polymerizable composition can be subjected to curing conditions such that a substantially complete cure is attained and wherein further exposure to curing conditions results in no significant further improvement in polymer properties, such as strength or hardness.

The present inventors have discovered reaction products or resins useful as cure accelerators for anaerobic compositions. The addition of such reaction products as cure accelerators into anaerobic adhesives as a replacement for some or all of the amount of conventional anaerobic cure accelerators (such as toluidine, acetyl phenylhydrazine and/or cumene hydroperoxide) surprisingly provides at least comparable cure speeds and physical properties for the reaction products formed therefrom, as compared with those observed from conventional anaerobic curable compositions. As such, these materials provide many benefits to anaerobic adhesive compositions, including but not limited to: reduced odor and safety concerns, reduced bioavailability, good formulation stability and good solubility in anaerobic curable compositions.

As noted above, in some non-limiting embodiments the present invention provides reaction product(s) prepared from (a) at least one (one or more) compounds selected from the group of compounds represented by structural Formula (I):

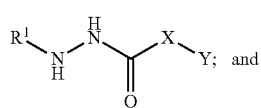

Formula (I)

(b) at least one (one or more) isocyanate functional materials.

In some non-limiting embodiments, the reaction product can have residual isocyanate functionality which can be further reacted with hydroxy, amino and/or thio functional materials, such as hydroxy, amino and/or thio functional acrylates, combinations thereof (such as acrylates having hydroxy and amino functionality), and mixtures thereof (such as hydroxy functional acrylate(s) and thio functional acrylate(s)), as discussed in detail below.

In the compounds of Formula (I) above, $R^1$ is selected from the group consisting of aryl and heteroaryl.

As used herein, "aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Non-limiting examples of useful heteroaryls include those containing about 5 to about 6 ring atoms. The "heteroaryl" can be optionally substituted by one or more "ring system substituents" which may be the same or different, and are as defined herein. The prefix aza, oxa or thia before the heteroaryl root name means that at least one of a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent. The phrase "optionally substituted" means optional substitution with the specified groups, radicals or moieties.

It should also be noted that any carbon as well as heteroatom with unsatisfied valences in the text, schemes, examples and Tables herein is assumed to have the sufficient number of hydrogen atom(s) to satisfy the valences.

When any variable (e.g., aryl, heterocycle, R², etc.) occurs more than one time in any constituent or in Formula I, etc., its definition on each occurrence is independent of its definition at every other occurrence.

In the compounds of Formula (I), X is selected from the group consisting of a direct bond, —O—, —S—, —NH—, alkylene, cycloalkylene, heterocyclylene, arylene, alkarylene, and heteroarylene. In some non-limiting embodiments, X is —O—.

As used herein, "alkylene" means a difunctional group obtained by removal of a hydrogen atom from an alkyl group such as is defined below. Non-limiting examples of alkylene groups include methylene, ethylene and propylene.

"Alkyl" means an aliphatic hydrocarbon group which may be straight or branched and comprising about 1 to about 20 carbon atoms in the chain, about 1 to about 12 carbon atoms in the chain, or about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)₂, carboxy and —C(O)O-alkyl. Non-limiting examples of suitable alkyl groups include methyl, ethyl, n-propyl, isopropyl and t-butyl.

"Heterocyclene" means a difunctional group obtained by removal of a hydrogen atom from a heterocyclyl group such as is defined below. "Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in heteroatom containing ring systems of this invention, there are no hydroxyl groups on carbon atoms adjacent to a N, O or S, as well as there are no N or S groups on carbon adjacent to another heteroatom. Thus, for example, in the ring:

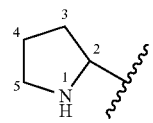

there is no —OH attached directly to carbons marked 2 and 5. It should also be noted that tautomeric forms such as, for example, the moieties:

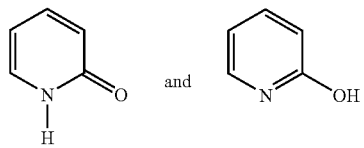

are considered equivalent in certain embodiments of this invention.

"Arylene" means a difunctional group obtained by removal of a hydrogen atom from an aryl group such as is defined above.

"Alkarylene" means a difunctional group obtained by removal of a hydrogen atom from an alkaryl group such as is defined below. "Alkaryl" or "alkylaryl" means an alkyl-aryl-group in which the alkyl and aryl are as previously described. Preferred alkylaryls comprise a lower alkyl group. A non-limiting example of a suitable alkylaryl group is tolyl. The bond to the parent moiety is through the aryl.

"Heteroarylene" means a difunctional group obtained by removal of a hydrogen atom from a heteroaryl group such as is defined above.

In the compounds of Formula (I), Y is a substituted alkylene group comprising an alkylene backbone having at least two contiguous carbon atoms. The alkylene group Y optionally can be interrupted by one or more —O—, —S—, or —NH— moieties, provided that each —O—, —S—, or —NH— moiety of Y, if present, is not adjacent to an —O—, —S—, or —NH— of X. The alkylene group of Y has substituents which are independently selected from the group consisting of —OH, —NH₂, —SH, cycloalkyl, heterocyclyl, aryl, and heteroaryl, or two hydrogen atoms on the same carbon atom of Y are replaced by carbonyl. As used herein, "cycloalkyl" means a non-aromatic mono- or multicyclic ring system comprising about 3 to about 10 carbon atoms, about 5 to about 10 carbon atoms, or about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

At least two substituents of Y are each independently selected from the group consisting of —OH, —NH₂, and —SH, provided that each of the —OH, —NH₂, -or —SH groups is not attached to the same carbon atom of Y or an —O—, —S—, or —NH— backbone moiety of Y. In some non-limiting embodiments, Y comprises two or three —OH substituents.

In some non-limiting embodiments, compound(s) according to Formula (I) are represented by structural Formula I(a) below:

Formula (I(a))

[Structure: R¹-NH-NH-C(=O)-O-Y]

wherein R¹ and Y are as described above.

In other non-limiting embodiments, compounds according to Formula (I) are represented by structural Formula I(b) and structural Formula I(c) as illustrated below:

Formula (I(b))

[Structure: R¹-NH-NH-C(=O)-X-CH(CH₂OH)-CH₂OH type]

Formula (I(c))

[Structure: R¹-NH-NH-C(=O)-X-CH₂-CH(OH)-CH₂OH]

wherein X and R¹ are as described above.

In one embodiment, a compound according to Formula (I) is represented by structural Formula (A):

Formula (A)

[Structure: phenyl-NH-NH-C(=O)-O-CH(CH₂OH)-CH₂OH]

In another embodiment, a compound according to Formula (I) is represented by structural Formula (B):

Formula (B)

[Structure: phenyl-NH-NH-C(=O)-O-CH(CH₂OH)-CH₂OH]

In another embodiment, a compound according to Formula (I) is represented by structural Formula (C):

Formula (C)

[Structure: phenyl-NH-NH-C(=O)-C(CH₃)(CH₂OH)-CH₂OH]

In another embodiment, a compound of the present invention according to Formula (I) is represented by structural Formula (D):

Formula (D)

[Structure: phenyl-NH-NH-C(=O)-CH₂CH₂-C(=O)-O-CH(CH₂OH)-CH₂OH]

Compounds of the present invention can be made by a variety of methods. In some non-limiting embodiments, the present invention provides reaction product(s) prepared from reactants comprising (1) the reaction product (A) prepared from reactants comprising (i) at least one compound selected from the group of compounds represented by structural Formula (II)

Formula (II)

[Structure: R¹-NH-NH₂ with additional H on nitrogens]

and (ii) at least one compound selected from the group of compounds represented by structural Formula (III) and structural Formula (IV):

Formula (III)

$$Y-X-\overset{O}{\underset{\|}{C}}-R^2$$

Formula (IV)

[Structure: cyclic with Z, Z', (R⁴)ₘ, ( )ₚ, C=O]; and (2) at least one isocyanate functional material.

In Formula II above, R¹ is selected from the group consisting of aryl and heteroaryl. In some non-limiting embodiments, R¹ is phenyl. A non-limiting example of a suitable compound of Formula (II) is phenylhydrazine, represented by structural Formula II(a):

Formula (II(a))

[Structure: phenyl-NH-NH₂]

In Formula III above, X is selected from the group consisting of a direct bond, —O—, —S—, —NH—, alkylene, cycloalkylene, heterocyclylene, arylene, alkarylene, and heteroarylene. In some non-limiting embodiments, X is —O—.

In Formula III, Y is a substituted alkylene group comprising an alkylene backbone having at least two contiguous carbon atoms and which optionally can be interrupted by one or more —O—, —S—, or —NH— moieties, provided that each —O—, —S—, or —NH— moiety of Y, if present, is not adjacent to an —O—, —S—, or —NH— of X. The alkylene group of Y has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl. At least two substituents of Y are each independently selected from the group consisting of —OH, —NH$_2$, and —SH, provided that each of the —OH, —NH$_2$, -or —SH groups is not attached to the same carbon atom of Y or an —O—, —S—, or —NH— backbone moiety of Y. $R^2$ is selected from the group consisting of —OH, —OR, NHR, alkyl, and arylalkyl, wherein R is an alkyl or an arylalkyl group. In some non-limiting embodiments, Y comprises two or three —OH substituents.

In some non-limiting embodiments, compound(s) of Formula (III) can be represented by Formulae (III(a)), (III(b)) or (III(c)):

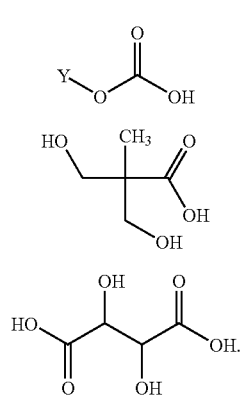

Formula (III(a))

Formula (III(b))

Formula (III(c))

pendant from the alkyl group or the aryl group of the arylalkyl, and heteroarylalkyl having at least one —OH, —NH$_2$, or —SH group pendant from the alkyl group or the aryl group of the heteroarylalkyl. In some non-limiting embodiments, $R^4$ is hydroxyalkyl. The variable p can be 1 or 2.

In some non-limiting embodiments, compound(s) of Formula (IV) can be represented by structural Formulae (IV(a)) or (IV(b)):

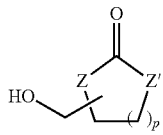

Formula (IV(a))

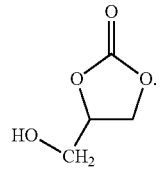

Formula (IV(b))

In some non-limiting embodiments, the reaction product (A) is prepared from phenylhydrazine and one or more of the above compounds of Formulae (III(b)), (III(c)) and/or (IV(b)).

In some non-limiting embodiments, the reaction product (A) is prepared from phenylhydrazine and glycerol carbonate as shown in the reaction scheme below:

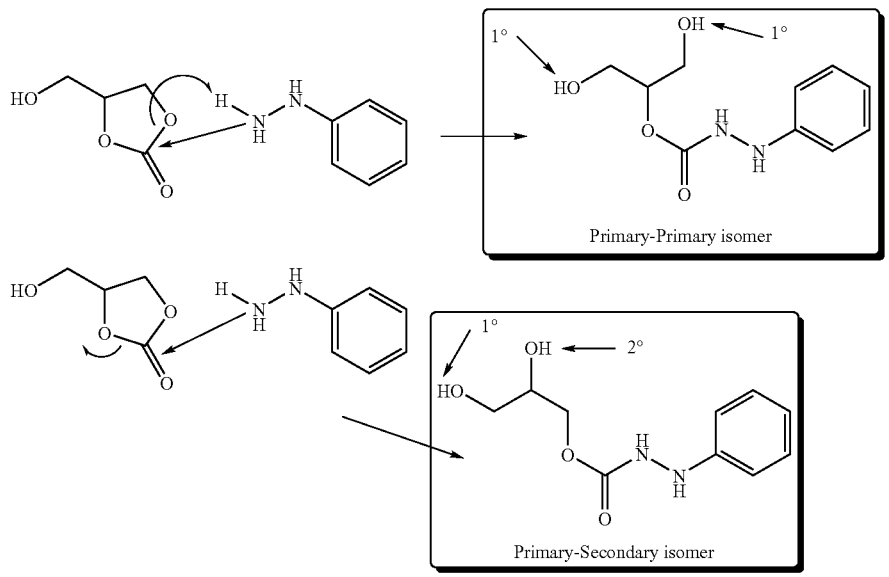

In Formula IV above, Z and Z' are each independently selected from the group consisting of —O—, —S—, and —N($R^3$)—, wherein $R^3$ is H or alkyl. The variable m is at least 1. In some non-limiting embodiments, m is 1 or 2. Each $R^4$ is independently selected from the group consisting of hydroxyalkyl, aminoalkyl, thioalkyl, hydroxyl substituted cycloalkyl, arylalkyl having at least one —OH, —NH$_2$, or —SH group In some non-limiting embodiments, there may be minor amounts of residual reactants, such as phenylhydrazine and glycerol carbonate, present with the final reaction product(s), for example less than about 5 weight percent, or less than about 1 weight percent, or free of residual reactants, based upon total weight of the reaction products and any residual reactants.

In another non-limiting embodiment, the reaction product (A) is prepared from phenylhydrazine and dimethylol propionic acid as shown in the reaction scheme below:

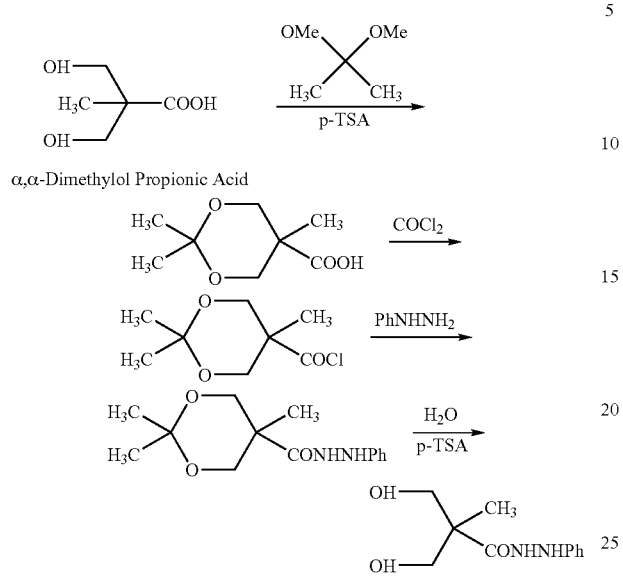

In another non-limiting embodiment, the reaction product (A) is prepared from phenylhydrazine and tartaric acid as shown in reaction scheme below:

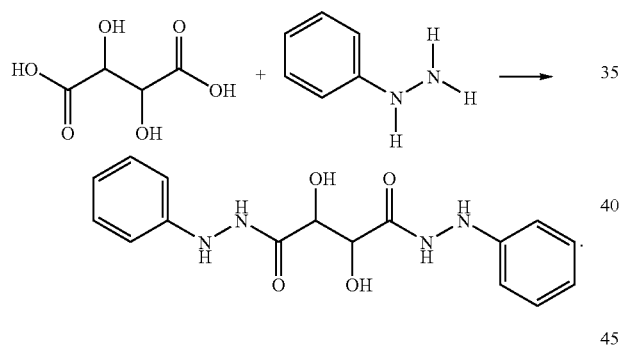

In some non-limiting embodiments, the molar ratio of compound(s) of Formula (II) to compound(s) of Formulae (III) and/or (IV) can range from about 5:1 to about 1:5, or about 3:1 to about 1:3, or about 1:1.

In some non-limiting embodiments, the reaction is conducted in the presence of a solvent. In some non-limiting embodiments, the compound of Formula (IV) is dissolved in solvent prior to reaction with the compound of Formula (II). Non-limiting examples of suitable solvents include, but are not limited to, mineral spirits, alcohols such as methanol, ethanol or butanol, aromatic hydrocarbons such as xylene, glycol ethers such as ethylene glycol monobutyl ether, esters, aliphatics, and mixtures of any of the foregoing. In some embodiments, residual solvent is extracted from the reaction product(s), for example by distillation or chromatography.

In some non-limiting embodiments, the reaction product(s) are purified to remove impurities, such as reaction by-products or impurities that accompany the reactants such as carriers. The reaction product(s) can be purified for example by filtration, stripping or chromatography, such that the purified reaction product(s) are essentially free of impurities, or comprise less than about 1 weight percent of impurities, or are free of impurities.

In some non-limiting embodiments, the reaction product (A) may be a compound of Formula (I), for example compounds represented by Formula (A) or Formula (B), or alternatively a mixture of compounds of Formula (I), for example a mixture of a compound represented by Formula (A) and a compound represented by structural Formula (B).

In other embodiments, the present invention provides reaction product(s) prepared from reactants comprising (1) at least one reaction product (B) prepared from reactants comprising (i) at least one compound selected from the group of compounds represented by structural Formula (V):

Formula (V)

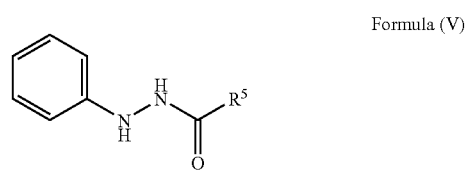

and (ii) at least one compound selected from the group of compounds represented by structural Formula (VI):

Formula (VI)

and
(ii) at least one isocyanate functional material.

In Formula V, $R^5$ is selected from the group consisting of hydroxyalkyl and carboxyalkyl. In one embodiment of the present invention, the reactant represented by Formula (V) is

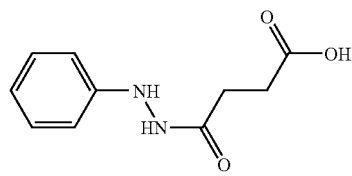

("SPH"), which is the reaction product of succinic anhydride and phenyl hydrazine and can be prepared according to U.S. Pat. No. 6,835,762, incorporated by reference herein.

In Formula VI, Z" is selected from the group consisting of —O—, —S—, and —NH—; q may be 1 to 4; $R^6$ may be independently selected from the group consisting of hydroxyalkyl, aminoalkyl, and thioalkyl; and n is at least 1. In another embodiment the reactant represented by Formula (VI) is:

In another non-limiting embodiment, the reaction product is prepared from SPH and glycidol as shown in the reaction scheme below:

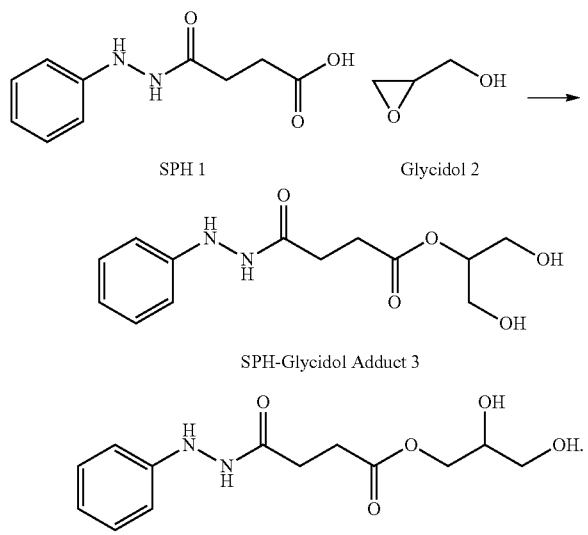

SPH 1  Glycidol 2

SPH-Glycidol Adduct 3

In some embodiments, reaction products of the above reactants SPH and glycidol can be represented by structural Formula (D1) and/or (D2):

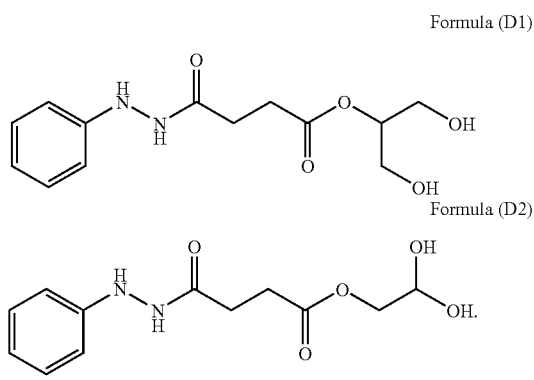

Formula (D1)

Formula (D2)

In some non-limiting embodiments, the molar ratio of compound(s) of Formula (V) to compound(s) of Formulae (VI) can range from about 5:1 to about 1:5, or about 3:1 to about 1:3, or about 1:1.

In some non-limiting embodiments, the reaction of compounds of Formula (V) and (VI) is conducted in the presence of a solvent. Suitable solvents and amounts are discussed in detail above.

In some non-limiting embodiments, the present invention provides methods of making reaction products from at least one isocyanate functional material and at least one compound(s) selected from the group of compounds represented by Formula (I):

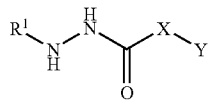

Formula (I)

by reacting at least one compound selected from the group of compounds represented by Formula (II):

Formula (II)

with at least one compound selected from the group of compounds represented by Formula (III) and Formula (IV):

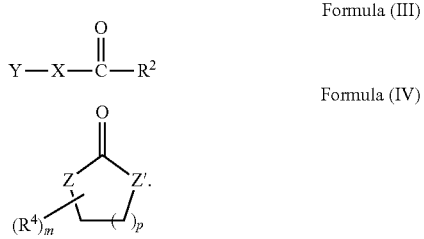

Formula (III)

Formula (IV)

and reacting the reaction product with at least one isocyanate functional material.

The reaction of compound(s) of Formula (II) and compound(s) of Formulae (III) and/or (IV) can be carried out in the presence of a solvent as discussed above. In some non-limiting embodiments, the compound(s) of Formulae (III) and/or (IV) can be solubilized in the solvent. The compound(s) of Formula (II) can be added to the mixture, allowed to exotherm and, if needed, heated at a temperature of about 0° C. to about 60° C., or about 60° C., for about 2 hours to about 7 days. The solvent can be removed by vacuum, if desired, for example at a temperature of about 60° C. and 100 torr and cooled, if desired.

As discussed generally above, the compound(s) of Formula (I), reaction product(s) (A) and/or reaction product(s) (B) are reacted with at least one isocyanate functional material.

In some non-limiting embodiments, the compound(s) of Formula (I), reaction product(s) (A) and/or reaction product(s) (B) can comprise about 5 to about 75 weight percent of the total weight of the reactants used for preparing the reaction product.

In some non-limiting embodiments, hydroxy functional compound(s) of Formula (I), reaction product(s) (A) and/or reaction product(s) (B) are reacted with isocyanate functional materials to form urethane linkages. In some non-limiting embodiments, the hydroxy functional compound(s) of Formula (I), reaction product(s) (A) and/or reaction product(s) (B) are reacted with polyisocyanate compound(s) to form an isocyanate functional urethane prepolymer and subsequently reacted with a reactive (meth)acrylate monomer, such as a hydroxy functional (meth)acrylate, to produce a di(meth)acrylate based polymer or resin which includes a functional accelerator moiety.

In some non-limiting embodiments, amino functional compound(s) of Formula (I), reaction product(s) (A) and/or reaction product(s) (B) are reacted with isocyanate functional materials to form urea linkages. In some non-limiting embodiments, the amino functional compound(s) of Formula (I), reaction product(s) (A) and/or reaction product(s) (B) are reacted with polyisocyanate compound(s) to form an isocyanate functional urea prepolymer and subsequently reacted with a reactive (meth)acrylate monomer, such as a hydroxy functional (meth)acrylate, to produce a di(meth)acrylate based polymer or resin which includes a functional accelerator moiety.

In some non-limiting embodiments, thiol functional compound(s) of Formula (I), reaction product(s) (A) and/or reaction product(s) (B) are reacted with isocyanate functional materials to form carbamothioate linkages. In some non-limiting embodiments, the thiol functional compound(s) of Formula (I), reaction product(s) (A) and/or reaction product(s) (B) are reacted with polyisocyanate compound(s) to form an isocyanate functional carbamothioate prepolymer and subsequently reacted with a reactive (meth)acrylate monomer, such as a hydroxy functional (meth)acrylate, to produce a di(meth)acrylate based polymer or resin which includes a functional accelerator moiety.

As used herein, the term "isocyanate functional material" includes compounds, monomers, oligomers and polymers comprising at least one or at least two —N═C═O functional groups and/or at least one or at least two —N═C═S (isothiocyanate) groups. Monofunctional isocyanates can be used as chain terminators or to provide terminal groups during polymerization. As used herein, "polyisocyanate" means an isocyanate comprising at least two —N═C═O functional groups, such as diisocyanates or triisocyanates, as well as dimers and trimers or biurets of the isocyanates, and mixtures thereof. Suitable isocyanates are capable of forming a covalent bond with a reactive group such as hydroxy functional group. Isocyanates useful in the present invention can be branched or unbranched.

Isocyanates useful in the present invention include "modified", "unmodified" and mixtures of "modified" and "unmodified" isocyanates. The isocyanates can have "free", "blocked" or partially blocked isocyanate groups. The term "modified" means that the aforementioned isocyanates are changed in a known manner to introduce biuret, urea, carbodiimide, urethane or isocyanurate groups or blocking groups. In some non-limiting embodiments, the "modified" isocyanate is obtained by cycloaddition processes to yield dimers and trimers of the isocyanate, i.e., polyisocyanates. Free isocyanate groups are extremely reactive. In order to control the reactivity of isocyanate group-containing components, the NCO groups may be blocked with certain selected organic compounds that render the isocyanate group inert to reactive hydrogen compounds at room temperature. When heated to elevated temperatures, e.g., ranging from about 90° C. to about 200° C., the blocked isocyanates release the blocking agent and react in the same way as the original unblocked or free isocyanate.

Generally, compounds used to block isocyanates are organic compounds that have active hydrogen atoms, e.g., volatile alcohols, epsilon-caprolactam or ketoxime compounds. Non-limiting examples of suitable blocking compounds include phenol, cresol, nonylphenol, epsilon-caprolactam and methyl ethyl ketoxime.

As used herein, the NCO in the NCO:OH ratio represents the free isocyanate of free isocyanate-containing materials, and of blocked or partially blocked isocyanate-containing materials after the release of the blocking agent. In some cases, it is not possible to remove all of the blocking agent. In those situations, more of the blocked isocyanate-containing material would be used to attain the desired level of free NCO.

The molecular weight of the isocyanate functional material can vary widely. In alternate non-limiting embodiments, the number average molecular weight (Mn) of each can be at least about 100 grams/mole, or at least about 150 grams/mole, or less than about 15,000 grams/mole, or less than about 5,000 grams/mole. The number average molecular weight can be determined using known methods, such as by gel permeation chromatography (GPC) using polystyrene standards.

Non-limiting examples of suitable isocyanate functional materials include aliphatic, cycloaliphatic, aromatic and heterocyclic isocyanates, dimers and trimers thereof, and mixtures thereof. When an aromatic polyisocyanate is used, generally care should be taken to select a material that does not cause the polyurethane to color (e.g., yellow).

In some non-limiting embodiments, the aliphatic and cycloaliphatic diisocyanates can comprise about 6 to about 100 carbon atoms linked in a straight chain or cyclized and having two isocyanate reactive end groups.

Non-limiting examples of suitable aliphatic isocyanates include straight chain isocyanates such as ethylene diisocyanate, trimethylene diisocyanate, 1,6-hexamethylene diisocyanate (HDI), tetramethylene diisocyanate, hexamethylene diisocyanate, octamethylene diisocyanate, nonamethylene diisocyanate, decamethylene diisocyanate, 1,6,11-undecanetriisocyanate, 1,3,6-hexamethylene triisocyanate, bis(isocyanatoethyl)-carbonate, and bis(isocyanatoethyl)ether.

Other non-limiting examples of suitable aliphatic isocyanates include branched isocyanates such as trimethylhexane diisocyanate, trimethylhexamethylene diisocyanate (TMDI), 2,2'-dimethylpentane diisocyanate, 2,2,4-trimethylhexane diisocyanate, 2,4,4,-trimethylhexamethylene diisocyanate, 1,8-diisocyanato-4-(isocyanatomethyl)octane, 2,5,7-trimethyl-1,8-diisocyanato-5-(isocyanatomethyl) octane, 2-isocyanatopropyl-2,6-diisocyanatohexanoate, lysinediisocyanate methyl ester and lysinetriisocyanate methyl ester.

Non-limiting examples of suitable cycloaliphatic isocyanates include dinuclear compounds bridged by an isopropylidene group or an alkylene group of 1 to 3 carbon atoms. Non-limiting examples of suitable cycloaliphatic isocyanates include 1,1'-methylene-bis-(4-isocyanatocyclohexane) or 4,4'-methylene-bis-(cyclohexyl isocyanate) (such as DESMODUR W commercially available from Bayer Corp.), 4,4'-isopropylidene-bis-(cyclohexyl isocyanate), 1,4-cyclohexyl diisocyanate (CHDI), 4,4'-dicyclohexylmethane diisocyanate, 3-isocyanato methyl-3,5,5-trimethylcyclohexyl isocyanate (a branched isocyanate also known as isophorone diisocyanate or IPDI) which is commercially available from Arco Chemical Co. and meta-tetramethylxylylene diisocyanate [a branched isocyanate also known as 1,3-bis(1-isocyanato-1-methylethyl)-benzene which is commercially available from Cytec Industries Inc. under the tradename TMXDI (Meta) Aliphatic Isocyanate] and mixtures thereof.

Other useful dinuclear cycloaliphatic diisocyanates include those formed through an alkylene group of from 1 to 3 carbon atoms inclusive, and which can be substituted with nitro, chlorine, alkyl, alkoxy and other groups that are not reactive with hydroxyl groups (or active hydrogens) providing they are not positioned so as to render the isocyanate group unreactive. Also, hydrogenated aromatic diisocyanates such as hydrogenated toluene diisocyanate may be used. Dinuclear diisocyanates in which one of the rings is saturated and the other unsaturated, which are prepared by partially hydrogenating aromatic diisocyanates such as diphenyl methane diisocyanates, diphenyl isopropylidene diisocyanate and diphenylene diisocyanate, may also be used.

Mixtures of cycloaliphatic diisocyanates with aliphatic diisocyanates and/or aromatic diisocyanates may also be used. An example is 4,4'-methylene-bis-(cyclohexyl isocyanate) with commercial isomer mixtures of toluene diisocyanate or meta-phenylene diisocyanate.

Thioisocyanates corresponding to the above diisocyanates can be used, as well as mixed compounds containing both an isocyanate and a thioisocyanate group.

Non-limiting examples of suitable isocyanate functional materials can include but are not limited to DESMODUR W, DESMODUR N 3300 (hexamethylene diisocyanate trimer), DESMODUR N 3400 (60% hexamethylene diisocyanate dimer and 40% hexamethylene diisocyanate trimer), which are commercially available from Bayer Corp.

Other non-limiting examples of suitable polyisocyanates include ethylenically unsaturated polyisocyanates; alicyclic polyisocyanates; aromatic polyisocyanates; aliphatic polyisocyanates; halogenated, alkylated, alkoxylated, nitrated, carbodiimide modified, urea modified and biuret modified derivatives of isocyanates; and dimerized and trimerized products of isocyanates.

Non-limiting examples of suitable ethylenically unsaturated polyisocyanates include butene diisocyanate and 1,3-butadiene-1,4-diisocyanate. Non-limiting examples of suitable alicyclic polyisocyanates include isophorone diisocyanate, cyclohexane diisocyanate, methylcyclohexane diisocyanate, bis(isocyanatomethyl) cyclohexane, bis(isocyanatocyclohexyl)methane, bis(isocyanatocyclohexyl)-2,2-propane, bis(isocyanatocyclohexyl)-1,2-ethane, 2-isocyanatomethyl-3-(3-isocyanatopropyl)-5-isocyanatomethyl-bicyclo[2.2.1]-heptane, 2-isocyanatomethyl-3-(3-isocyanatopropyl)-6-isocyanatomethyl-bicyclo[2.2.1]-heptane, 2-isocyanatomethyl-2-(3-isocyanatopropyl)-5-isocyanatomethyl-bicyclo[2.2.1]-heptane, 2-isocyanatomethyl-2-(3-isocyanatopropyl)-6-isocyanatomethyl-bicyclo[2.2.1]-heptane, 2-isocyanatomethyl-3-(3-isocyanatopropyl)-6-(2-isocyanatoethyl)-bicyclo[2.2.1]-heptane, 2-isocyanatomethyl-2-(3-isocyanatopropyl)-5-(2-isocyanatoethyl)-bicyclo[2.2.1]-heptane and 2-isocyanatomethyl-2-(3-isocyanatopropyl)-6-(2-isocyanatoethyl)-bicyclo[2.2.1 ]-heptane.

Non-limiting examples of suitable aromatic polyisocyanates include α,α'-xylene diisocyanate, bis(isocyanatoethyl) benzene, α,α,α',α'-tetramethylxylene diisocyanate, 1,3-bis (1-isocyanato-1-methylethyl)benzene, bis(isocyanatobutyl) benzene, bis(isocyanatomethyl)naphthalene, bis(isocyanatomethyl)diphenyl ether, bis(isocyanatoethyl) phthalate, mesitylene triisocyanate and 2,5-di (isocyanatomethyl)furan, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene diisocyanate, benzene triisocyanate, naphthalene diisocyanate, methylnaphthalene diisocyanate, biphenyl diisocyanate, toluidine diisocyanate, tolylidine diisocyanate, tolylene diisocyanate, 4,4'-diphenylmethane diisocyanate, bis(3-methyl-4-isocyanatophenyl) methane, bis(isocyanatophenyl)ethylene, 3,3'-dimethoxy-biphenyl-4,4'-diisocyanate, triphenylmethane triisocyanate, polymeric 4,4'-diphenylmethane diisocyanate, naphthalene triisocyanate, diphenylmethane-2,4,4'-triisocyanate, 4-methyldiphenylmethane-3,5,2',4',6'-pentaisocyanate, diphenylether diisocyanate, bis(isocyanatophenylether)ethyleneglycol, bis(isocyanatophenylether)-1,3-propyleneglycol, benzophenone diisocyanate, carbazole diisocyanate, ethylcarbazole diisocyanate and dichlorocarbazole diisocyanate.

In some non-limiting embodiments, the isocyanate functional material comprises at least one triisocyanate or at least one polyisocyanate trimer. Non-limiting examples of such isocyanates include aromatic triisocyanates such as tris(4-iso-cyanatophenyl)methane (DESMODUR R), 1,3,5-tris(3-isocyanato-4-methylphenyl)-2,3,6-trioxohexahydro-1,3,5 triazine (DESMODUR IL); adducts of aromatic diisocyanates such as the adduct of 2,4-tolylene diisocyanate (TDI, 2,4-diisocyanatotoluene) and trimethylolpropane (DESMO-DUR L); and from aliphatic triisocyanates such as N-isocyanatohexylaminocarbonyl-N,N'-bis(isocyanatohexyl)urea (DESMODUR N), 2,4,6-trioxo-1,3,5-tris(6-isocyanatohexyl)hexahydro-1,3,5-triazine (DESMODUR N3390), 2,4,6-trioxo-1,3,5-tris(5-isocyanato-1,3,3-trimethylcyclo-hexylmethyl)hexahydro-1,3,5-triazine (DESMODUR Z4370), and 4-(isocyanatomethyl)-1,8-octane diisocyanate. The above DESMODUR products are commercially available from Bayer Corp. Also useful are the biuret of hexanediisocyanate, polymeric methane diisocyanate, and polymeric isophorone diisocyanate. Trimers of hexamethylene diisocyanate, isophorone diisocyanate and tetramethylxylylene diisocyanate In some non-limiting embodiments, the isocyanate functional material is a cycloaliphatic compound, such as a dinuclear compound bridged by an isopropylidene group or an alkylene group of 1 to 3 carbon atoms.

In some non-limiting embodiments, the isocyanate functional material is a diisocyanate, such as methylene bis(phenyl isocyanate) (also known as MDI); 2,4-toluene diisocyanate (2,4-TDI); a 80:20 mixture of 2,4- and 2,6-toluene diisocyanate (also known as TDI); 3-isocyanatomethyl-3,5, 5-trimethyl cyclohexylisocyanate (IPDI); m-tetramethyl xylene diisocyanate (TMXDI); hexamethylene diisocyanate (HDI); and 4,4'-methylene-bis-(cyclohexyl isocyanate) (commercially available as Desmodur W).

In some non-limiting embodiments, the isocyanate functional materials can comprise isocyanate functional (meth) acrylates.

In some non-limiting embodiments, the isocyanate functional material can comprise about 5 to about 50 weight percent of the total weight of the reactants used for preparing the reaction product, or about 15 to about 30 weight percent, or about 25 weight percent.

In some non-limiting embodiments, the reaction product(s) of the hydroxy-, amino- and/or thio functional compound(s) discussed above with isocyanate functional material(s) can have residual isocyanate functionality.

In some non-limiting embodiments, the reaction product of the hydroxy-, amino- and/or thio functional compound(s) with isocyanate functional material(s) can have a number average molecular weight of about 100 to about 20,000 grams/mole, or about 500 to about 5,000 grams/mole.

In some non-limiting embodiments, the reactants can further comprise at least one functional material selected from the group consisting of hydroxy-, amino- and/or thio functional materials. These functional materials can be reacted with the hydroxy-, amino- and/or thio functional compound(s) and the isocyanate functional material(s) concurrently or post-reacted with the reaction product of the hydroxy-, amino- and/or thio functional compound(s) and the isocyanate functional material(s), as desired.

Non-limiting examples of suitable hydroxy functional materials include hydroxy functional (meth)acrylates and hydroxy functional vinyl ethers.

The phrase "hydroxyl-functional (meth)acrylate" means any hydroxyl-substituted acrylate or methacrylate compound that would be suitable for making and using a capped urethane material. Non-limiting examples of suitable hydroxy functional (meth)acrylates include hydroxyethyl acrylate, hydroxypropyl acrylate, hydroxybutyl acrylate, hydroxyethyl methacrylate, hydroxypropyl methacrylate, hydroxybutyl methacrylate and mixtures thereof. Other non-limiting examples of suitable hydroxy functional (meth)acrylates include 2-hydroxyethyl acrylate, 2-hydroxypropyl acrylate, 2-hydroxyethyl methacrylate, pentaerythritol triacrylate (PETA), and 4-hydroxybutyl acrylate.

The phrase "hydroxy functional vinyl ether" means any hydroxy-substituted vinyl ether that would be suitable for making and using a capped urethane oligomer. Non-limiting examples of suitable hydroxy functional vinyl ethers can be selected from the group consisting of hydroxyethyl vinyl ethers, hydroxypropyl vinyl ethers, hydroxybutyl vinyl ethers and mixtures thereof, such as ethylene glycol monovinyl ether, and cyclohexane dimethanol monovinyl ether.

In some non-limiting embodiments, the hydroxy-functional material having at least one acrylate group can have a number average molecular weight of about 80 to about 1,000 grams/mole, or about 100 to about 800 grams/mole, or about 110 to about 600 grams/mole.

In some non-limiting embodiments, the hydroxy-functional material having at least one acrylate group can comprise about 1 to about 30 weight percent of the reactants used for preparing the urethane, or about 2 to about 15 weight percent of the reactants, or about 3 to about 12 weight percent of the reactants.

The reaction products of the present invention can have a number average molecular weight ranging from about 500 to about 10,000 grams/mole, or about 1000 to about 7000 grams/mole.

Anaerobic curable compositions generally are based on a (meth)acrylate component, together with an anaerobic cure-inducing composition. In some non-limiting embodiments, the anaerobic curable composition of the present invention is based on the (meth)acrylate component, together with an anaerobic cure-inducing composition, which preferably has at least reduced levels of APH (such as about 50% or less by weight of that which is used in conventional anaerobic curable compositions), is substantially free of APH (less than about 10 weight percent, less than about 5 weight percent or less than about 1 weight percent) or is free of APH. In place of some or all of APH is the inventive cure accelerator, such as compounds of Formula I or the above reaction products.

(Meth)acrylate monomers suitable for use as the (meth)acrylate component in the present invention may be selected from a wide variety of materials, such as those represented by $H_2C=CGCO_2R^8$, where G may be hydrogen, halogen or alkyl groups having from 1 to about 4 carbon atoms, and $R^8$ may be selected from alkyl, cycloalkyl, alkenyl, cycloalkenyl, alkaryl, aralkyl or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone and the like.

Additional (meth)acrylate monomers suitable for use herein include polyfunctional (meth)acrylate monomers, for example di-or tri-functional (meth)acrylates such as polyethylene glycol di(meth)acrylates, tetrahydrofuran(meth)acrylates and di(meth)acrylates, hydroxypropyl(meth)acrylate ("HPMA"), hexanediol di(meth)acrylate, trimethylol propane tri(meth)acrylates ("TMPTMA"), diethylene glycol dimethacrylate, triethylene glycol dimethacrylates ("TRIEGMA"), tetraethylene glycol di(meth)acrylates, dipropylene glycol di(meth)acrylates, di-(pentamethylene glycol) di(meth)acrylates, tetraethylene diglycol di(meth)acrylates, diglycerol tetra(meth)acrylates, tetramethylene di(meth) acrylates, ethylene di(meth)acrylates, neopentyl glycol di(meth)acrylates, and bisphenol-A mono and di(meth)acrylates, such as ethoxylated bisphenol-A (meth)acrylate ("EBIPMA"), and bisphenol-F mono and di(meth)acrylates, such as ethoxylated bisphenol-A (meth)acrylate.

Still other (meth)acrylate monomers that may be used herein include silicone (meth)acrylate moieties ("SiMA"), such as those taught by and claimed in U.S. Pat. No. 5,605,999 (Chu), incorporated herein by reference.

Other suitable monomers include polyacrylate esters represented by the formula

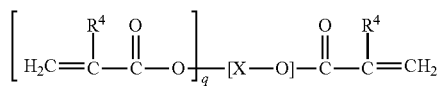

wherein $R^4$ is a radical selected from the group consisting of hydrogen, halogen and alkyl of from 1 to about 4 carbon atoms; q is an integer equal to at least 1, and preferably equal to from 1 to about 4; and X is an organic radical containing at least two carbon atoms and having a total bonding capacity of q plus 1. With regard to the upper limit for the number of carbon atoms in X, workable monomers exist at essentially any value. As a practical matter, however, a general upper limit is about 50 carbon atoms, preferably 30, and most preferably about 20.

For example, X can be an organic radical of the formula:

wherein each of $Y^1$ and $Y^2$ is an organic radical, preferably a hydrocarbon group, containing at least 2 carbon atoms, and preferably from 2 to about 10 carbon atoms, and Z is an organic radical, preferably a hydrocarbon group, containing at least 1 carbon atom, and preferably from 2 to about 10 carbon atoms.

Other classes of useful monomers are the reaction products of di- or tri-alkylolamines (e.g., ethanolamines or propanolamines) with acrylic acids, such as are disclosed in French Pat. No. 1,581,361.

Non-limiting examples of useful acrylic ester oligomers include those having the following general formula:

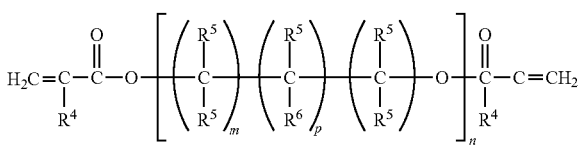

wherein $R^5$ represents a radical selected from the group consisting of hydrogen, lower alkyl of from 1 to about 4 carbon atoms, hydroxy alkyl of from 1 to about 4 carbon atoms, and

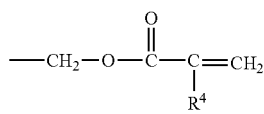

wherein $R^4$ is a radical selected from the group consisting of hydrogen, halogen, and lower alkyl of from 1 to about 4 carbon atoms; $R^6$ is a radical selected from the group consisting of hydrogen, hydroxyl, and

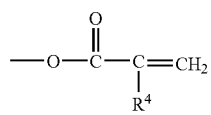

m is an integer equal to at least 1, e.g., from 1 to about 15 or higher, and preferably from 1 to about 8; n is an integer equal to at least 1, e.g., 1 to about 40 or more, and preferably between about 2 and about 10; and p is 0 or 1.

Typical examples of acrylic ester oligomers corresponding to the above general formula include di-, tri- and tetraethyleneglycol dimethacrylate; di(pentamethyleneglycol) dimethacrylate; tetraethyleneglycol diacrylate; tetraethyleneglycol di(chloroacrylate); diglycerol diacrylate; diglycerol tetramethacrylate; butyleneglycol dimethacrylate; neopentylglycol diacrylate; and trimethylolpropane triacrylate.

While di- and other polyacrylate esters, and particularly the polyacrylate esters described in the preceding paragraphs, can be desirable, monofunctional acrylate esters (esters containing one acrylate group) also may be used. When dealing with monofunctional acrylate esters, it is highly preferable to use an ester which has a relatively polar alcoholic moiety. Such materials are less volatile than low molecular weight alkyl esters and, more important, the polar group tends to provide intermolecular attraction during and after cure, thus producing more desirable cure properties, as well as a more durable sealant or adhesive. Most preferably, the polar group is selected from the group consisting of labile hydrogen, heterocyclic ring, hydroxy, amino, cyano, and halo polar groups. Typical examples of compounds within this category are cyclohexylmethacrylate, tetrahydrofurfuryl methacrylate, hydroxyethyl acrylate, hydroxypropyl methacrylate, t-butylaminoethyl methacrylate, cyanoethylacrylate, and chloroethyl methacrylate.

Another useful class of monomers is prepared by the reaction of a monofunctionally substituted alkyl or aryl acrylate ester containing an active hydrogen atom on the functional substituent. This monofunctional, acrylate-terminated material is reacted with an organic polyisocyanate in suitable proportions so as to convert all of the isocyanate groups to urethane or ureido groups. The monofunctional alkyl and aryl acrylate esters are preferably the acrylates and methacrylates containing hydroxy or amino functional groups on the nonacrylate portion thereof. Acrylate esters suitable for use have the formula

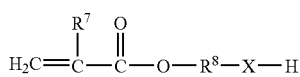

wherein X is selected from the group consisting of —O— and

and $R^9$ is selected from the group consisting of hydrogen and lower alkyl of 1 through 7 carbon atoms; $R^7$ is selected from the class consisting of hydrogen, chlorine and methyl and ethyl radicals; and $R^8$ is a divalent organic radical selected from the group consisting of lower alkylene of 1 through 8 carbon atoms, phenylene and naphthylene. These groups upon proper reaction with a polyisocyanate, yield a monomer of the following general formula:

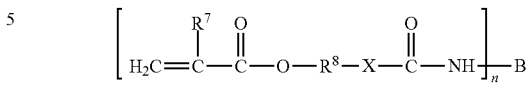

wherein n is an integer from 2 to about 6; B is a polyvalent organic radical selected from the group consisting of alkyl, alkenyl, cycloalkyl, cycloalkenyl, aryl, aralkyl, alkaryl and heterocyclic radicals both substituted and unsubstituted; and $R^7$, $R^8$ and X have the meanings given above.

The hydroxy- and amine-containing materials suitable for use in the preparation of the above monomeric products are exemplified by, but not limited to, such materials as hydroxyethyl acrylate, hydroxyethyl methacrylate, aminoethyl methacrylate, 3-hydroxypropyl methacrylate, aminopropyl methacrylate, hydroxyhexyl acrylate, t-butylaminoethyl methacrylate, hydroxyoctyl methacrylate, and the like.

The preferred organic polyisocyanates comprise the higher alkenyl diisocyanates, the cycloalkenyl diisocyanates and the aromatic diisocyanates containing 8 or more carbon atoms and preferably from 8 to about 30 carbon atoms, such as, for example, octamethylene diisocyanate, durene diisocyanate, 4,4'-diphenyldiisocyanate, and toluene diisocyanate.

The proportions in which the reactants may be combined can be varied somewhat; however, it is generally preferred to employ the reactants in chemically equivalent amounts up to a slight excess, e.g., 1 equivalent excess of the polyisocyanate. As used herein the expression "chemically equivalent amount" refers to the amount needed to furnish one isocyanate group per hydroxy or amino group.

The reaction may be accomplished in the presence or absence of diluents. Preferably diluents which include the hydrocarbons, such as aliphatic, cycloaliphatic and aromatic hydrocarbons, for example, benzene, toluene, cyclohexane, hexane, heptane and the like, are employed but other diluents, such as methyl isobutyl ketone, diamyl ketone, isobutyl methacrylate, triethyleneglycol dimethacrylate, and cyclohexyl methacrylate can also be beneficially utilized, if desired, especially where complete compatibility with the sealant system is desired.

The temperature employed in the reaction may also vary over a wide range. Where the components are combined in approximately chemical equivalent amounts or with slight excess of the isocyanate reactant, useful temperatures may vary from room temperature or below, e.g., 10° C. to 15° C., up to and including temperatures of 100° C. to 175° C. Where reacting the simpler isocyanates, the components are preferably combined at or near room temperature, such as temperatures ranging from 20° C. to 30° C. In the preparation of the high molecular weight isocyanate adducts using an excess of the isocyanate, the reactants may be combined at room temperature or preferably heated at temperatures ranging from about 40° C. to about 150° C. Reactions conducted at about 90° C. to 120° C. have been found to proceed quite smoothly.

Of course, combinations of these (meth)acrylate monomers may also be used.

The (meth)acrylate component can comprise from about 10 to about 90 percent by weight of the composition, such as about 60 to about 90 percent by weight, based on the total weight of the composition.

In some non-limiting embodiments, the reactants can further comprise at least one polyol. As used herein, the term "polyol" includes compounds, monomers, oligomers and polymers comprising at least two hydroxyl groups (such as diols) or at least three hydroxyl groups (such as triols), higher functional polyols and mixtures thereof. Suitable polyols are capable of forming a covalent bond with a reactive group such as an isocyanate functional group.

Non-limiting examples of suitable polyols include hydrocarbon polyols, polyether polyols, polyester polyols and mixtures thereof. As used herein, hydrocarbon polyol means saturated aliphatic polyols, unsaturated aliphatic polyols such as olefins, alicyclic polyols and aromatic polyols.

Non-limiting examples of suitable diols include straight chain alkane diols such as ethylene glycol, diethylene glycol, triethylene glycol, tetraethylene glycol, 1,2-ethanediol, propane diols such as 1,2-propanediol and 1,3-propanediol, butane diols such as 1,2-butanediol, 1,3-butanediol, and 1,4-butanediol, pentane diols such as 1,5-pentanediol, 1,3-pentanediol and 2,4-pentanediol, hexane diols such as 1,6-hexanediol and 2,5-hexanediol, heptane diols such as 2,4-heptanediol, octane diols such as 1,8-octanediol, nonane diols such as 1,9-nonanediol, decane diols such as 1,10-decanediol, dodecane diols such as 1,12-dodecanediol, octadecanediols such as 1,18-octadecanediol, sorbitol, mannitol, and mixtures thereof. In some non-limiting embodiments, the diol is a propane diol such as 1,2-propanediol and 1,3-propanediol, or butane diol such as 1,2-butanediol, 1,3-butanediol, and 1,4-butanediol. In some non-limiting embodiments, one or more carbon atoms in the polyol can be replaced with one or more heteroatoms, such as N, S, or O, for example sulfonated polyols, such as dithio-octane bis diol, thiodiethanol such as 2,2-thiodiethanol, or 3,6-dithia-1,2-octanediol.

Other non-limiting examples of suitable diols include those represented by the following formula:

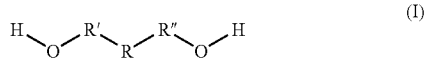

(I)

wherein R represents $C_0$ to $C_{18}$ divalent linear or branched aliphatic, cycloaliphatic, aromatic, heterocyclic, or oligomeric saturated alkylene radical or mixtures thereof; $C_2$ to $C_{18}$ divalent organic radical containing at least one element selected from the group consisting of sulfur, oxygen and silicon in addition to carbon and hydrogen atoms; $C_5$ to $C_{18}$ divalent saturated cycloalkylene radical; or $C_5$ to $C_{18}$ divalent saturated heterocycloalkylene radical; and R' and R" can be present or absent and, if present, each independently represent $C_1$ to $C_{18}$ divalent linear or branched aliphatic, cycloaliphatic, aromatic or aryl, heterocyclic, polymeric, or oligomeric saturated alkylene radical or mixtures thereof.

Other non-limiting examples of suitable diols include branched chain alkane diols, such as propylene glycol, dipropylene glycol, tripropylene glycol, neopentyl glycol, 2-methyl-butanediol. 2,2,4-trimethyl-1,3-pentanediol, 2-methyl-1,3-pentanediol, 2-ethyl-1,3-hexanediol, 2-methyl-1,3-propanediol, 2,2-dimethyl-1,3-propanediol, dibutyl 1,3-propanediol, polyalkylene glycols such as polyethylene glycols, and mixtures thereof.

In some non-limiting embodiments, the diol can be a cycloalkane diol, such as cyclopentanediol, 1,4-cyclohexanediol, cyclohexanedimethanols (CHDM), such as 1,4-cyclohexanedimethanol, cyclododecanediol, 4,4'-isopropylidene-biscyclohexanol, hydroxypropylcyclohexanol, cyclohexanediethanol, 1,2-bis(hydroxymethyl)-cyclohexane, 1,2-bis(hydroxyethyl)-cyclohexane, 4,4'-isopropylidene-biscyclohexanol, bis(4-hydroxycyclohexanol)methane, and 4,8-bis(hydroxymethyl)tricyclo[5.2.1.0$^{2,6}$]decane and mixtures thereof.

In some non-limiting embodiments, the diol can be an aromatic diol, such as dihydroxybenzene, 1,4-benzenedimethanol, xylene glycol, hydroxybenzyl alcohol and dihydroxytoluene; bisphenols, such as, 4,4'-isopropylidenediphenol (Bisphenol A), 4,4'-oxybisphenol, 4,4'-dihydroxybenzophenone, 4,4'-thiobisphenol, phenolphthalein, bis(4-hydroxyphenyl)methane, 4,4'-(1,2-ethenediyl)bisphenol and 4,4'-sulfonylbisphenol; hydrogenated bisphenols, halogenated bisphenols, such as 4,4'-isopropylidenebis(2,6-dibromophenol), 4,4'-isopropylidenebis(2,6-dichlorophenol) and 4,4'-isopropylidenebis(2,3,5,6-tetrachlorophenol); alkoxylated bisphenols, which can have, for example, ethoxy, propoxy, α-butoxy and β-butoxy groups; and biscyclohexanols, which can be prepared by hydrogenating the corresponding bisphenols, such as 4,4'-isopropylidene-biscyclohexanol, 4,4'-oxybiscyclohexanol, 4,4'-thiobiscyclohexanol and bis(4-hydroxycyclohexanol)methane, the alkoxylation product of 1 mole of 2,2-bis(4-hydroxyphenyl)propane (i.e., bisphenol-A) and 2 moles of propylene oxide, hydroxyalkyl terephthalates such as meta or para bis(2-hydroxyethyl)terephthalate, bis(hydroxyethyl)hydroquinone and mixtures thereof.

In some non-limiting embodiments, the diol can be an heterocyclic diol, for example a dihydroxy piperidine such as 1,4-bis(hydroxyethyl)piperazine; a diol of an amide or alkane amide [such as ethanediamide (oxamide)], for example N,N', bis(2-hydroxyethyl)oxamide; a diol of a propionate, such as 2,2-dimethyl-3-hydroxypropyl-2,2-dimethyl-3-hydroxypropionate; a diol of a hydantoin, such as bishydroxypropyl hydantoin; a diol of a phthalate, such as meta or para bis(2-hydroxyethyl)terephthalate; a diol of a hydroquinone, such as a dihydroxyethylhydroquinone; and/or a diol of an isocyanurate, such as dihydroxyethyl isocyanurate.

Non-limiting examples of trifunctional, tetrafunctional or higher polyols suitable for use include branched chain alkane polyols such as glycerol or glycerin, tetramethylolmethane, trimethylolethane (for example 1,1,1-trimethylolethane), trimethylolpropane (TMP) (for example 1,1,1-trimethylolpropane), erythritol, pentaerythritol, dipentaerythritol, tripentaerythritol, sorbitan, alkoxylated derivatives thereof (discussed below) and mixtures thereof.

In some non-limiting embodiments, the polyol can be a cycloalkane polyol, such as trimethylene bis(1,3,5-cyclohexanetriol); or an aromatic polyol, such as trimethylene bis(1,3,5-benzenetriol).

Further non-limiting examples of suitable polyols include the aforementioned polyols which can be alkoxylated derivatives, such as ethoxylated, propoxylated and butoxylated. In alternate non-limiting embodiments, the following polyols can be alkoxylated with from 1 to 10 alkoxy groups: glycerol, trimethylolethane, trimethylolpropane, benzenetriol, cyclohexanetriol, erythritol, pentaerythritol, sorbitol, mannitol, sorbitan, dipentaerythritol and tripentaerythritol. Non-limiting examples of suitable alkoxylated polyols include ethoxylated trimethylolpropane, propoxylated trimethylolpropane, ethoxylated trimethylolethane, and mixtures thereof.

In some non-limiting embodiments, the polyol can be an unsaturated aliphatic polyol such as NISSO GI-1000 hydroxy terminated, hydrogenated 1,2-polybutadiene (HPBD resin) having a calculated number average molecular weight of about 1500 and a hydroxyl value of about 60-120 KOH mg/g commercially available from Nippon Soda Co Ltd.

In some non-limiting embodiments, the polyol for use in the present invention can be an SH-containing material, such as a dithiol or polythiol. Non-limiting examples of suitable polythiols can include, but are not limited to, aliphatic polythiols, cycloaliphatic polythiols, aromatic polythiols, heterocyclic polythiols, polymeric polythiols, oligomeric polythiols and mixtures thereof. As used herein, the terms "thiol," "thiol group," "mercapto" or "mercapto group" refer to an —SH group which is capable of forming a thiourethane linkage, (i.e., —NH—C(O)—S—) with an isocyanate group or a dithiourethane linkage (i.e., —NH—C(S)—S—) with an isothiocyanate group.

In some non-limiting embodiments, the polyol can be one or more polyether polyol(s). Non-limiting examples of polyether polyols include poly(oxyalkylene) polyols or polyalkoxylated polyols. Poly(oxyalkylene) polyols can be prepared in accordance with known methods. In a non-limiting embodiment, a poly(oxyalkylene) polyol can be prepared by condensing an alkylene oxide, or a mixture of alkylene oxides, using an acid- or base-catalyzed addition with a polyhydric initiator or a mixture of polyhydric initiators, such as ethylene glycol, propylene glycol, glycerol, and sorbitol. Compatible mixtures of polyether polyols can also be used. As used herein, "compatible" means that two or more materials are mutually soluble in each other so as to essentially form a single phase. Non-limiting examples of alkylene oxides can include ethylene oxide, propylene oxide, butylene oxide, amylene oxide, aralkylene oxides, such as styrene oxide, mixtures of ethylene oxide and propylene oxide. In some non-limiting embodiments, polyoxyalkylene polyols can be prepared with mixtures of alkylene oxide using random or step-wise oxyalkylation. Non-limiting examples of such poly(oxyalkylene) polyols include polyoxyethylene polyols, such as polyethylene glycol, and polyoxypropylene polyols, such as polypropylene glycol.

Other polyether polyols include block polymers such as those having blocks of ethylene oxide-propylene oxide and/or ethylene oxide-butylene oxide. In some non-limiting embodiments, the polyether polyol comprises a block copolymer of the following formula:

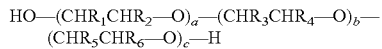

where $R_1$ through $R_6$ can each independently represent hydrogen or methyl; and a, b, and c can each be independently selected from an integer from 0 to 300, wherein a, b, and c are selected such that the number average molecular weight of the polyol is less than about 32,000 grams/mole, or less than about 10,000 grams/mole, as determined by GPC.

In some non-limiting embodiments, polyalkoxylated polyols can be represented by the following general formula:

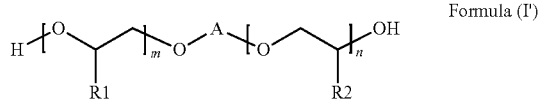

Formula (I')

wherein m and n can each be a positive integer, the sum of m and n being from 5 to 70; $R_1$ and $R_2$ are each hydrogen, methyl or ethyl; and A is a divalent linking group such as a straight or branched chain alkylene which can contain from 1 to 8 carbon atoms, phenylene, and $C_1$ to $C_9$ alkyl-substituted phenylene. The values of m and n can, in combination with the selected divalent linking group, determine the molecular weight of the polyol. Polyalkoxylated polyols can be prepared by methods that are known in the art. In a non-limiting embodiment, a polyol such as 4,4'-isopropylidenediphenol can be reacted with an oxirane-containing material such as ethylene oxide, propylene oxide or butylene oxide, to form what is commonly referred to as an ethoxylated, propoxylated or butoxylated polyol having hydroxyl functionality.

In some non-limiting embodiments, the polyether polyol can be PLURONIC ethylene oxide/propylene oxide block copolymers, such as PLURONIC R and PLURONIC L62D, and/or TETRONIC tetra-functional block copolymers based on ethylene oxide and propylene oxide, such as TETRONIC R, which are commercially available from BASF Corp.

As used herein, the phrase "polyether polyols" also can include poly(oxytetramethylene)diols prepared by the polymerization of tetrahydrofuran in the presence of Lewis acid catalysts such as, but not limited to boron trifluoride, tin (IV) chloride and sulfonyl chloride.

In some non-limiting embodiments, non-limiting examples of suitable polyether polyols include poly(propylene oxide)diols, copoly(ethylene oxide-propylene oxide)diols, and poly(tetramethylene oxide)diols.

In some non-limiting embodiments, the polyether polyol can be POLYMEG® 2000 polytetramethylene ether glycol (linear diol having a backbone of repeating tetramethylene units connected by ether linkages and capped with primary hydroxyls having a molecular weight of about 1900-2100 and a hydroxyl number of about 53.0 to about 59.0), commercially available from Lyondell.

In other embodiments, the polyether polyol can be TERATHANE® 1000 polytetramethylene ether glycol is a blend of linear diols in which the hydroxyl groups are separated by repeating tetramethylene ether groups: $HO(CH_2CH_2CH_2CH_2$—O—$)_n$H in which n averages 14 and having a hydroxyl number of 107-118, commercially available from INVISTA, or POLYMEG® 1000.

In some non-limiting embodiments, the polyol can be one or more polyester polyol(s). In some non-limiting embodiments, the polyester polyol is selected from the group consisting of polyester glycols, polycaprolactone polyols, polycarbonate polyols and mixtures thereof. Non-limiting examples of suitable polyester polyols include any well-known di-, tri-, or tetrahydroxy-terminated polyesters such as polylactone polyesters and polyester polyols produced by the polycondensation reactions of dicarboxylic acids or their anhydrides with di-, tri-, or tetra-alcohols.

Non-limiting examples of such polyester polyols include polyester glycols, polycaprolactone polyols, polycarbonate polyols and mixtures thereof. Polyester glycols can include the esterification products of one or more dicarboxylic acids having from four to ten carbon atoms, such as, but not limited to adipic, succinic or sebacic acids, with one or more low molecular weight glycols having from two to ten carbon atoms, such as, but not limited to ethylene glycol, propylene glycol, diethylene glycol, 1,4-butanediol, neopentyl glycol, 1,6-hexanediol and 1,10-decanediol. Esterification procedures for producing polyester polyols are described, for example, in the article D. M. Young et al., "Polyesters from Lactone," Union Carbide F-40, p. 147.

Non-limiting examples of polycaprolactone polyols include those prepared by condensing caprolactone in the presence of difunctional active hydrogen material such as water or low molecular weight glycols, for example ethylene glycol and propylene glycol. Non-limiting examples of suitable polycaprolactone polyols can include CAPA polycaprolactone polyols commercially available from Solvay Chemical of Houston, Tex., such as CAPA 2085 linear polyester diol derived from caprolactone monomer, terminated by primary hydroxyl groups, and having a mean molecular weight of 830 and a typical OH value of 135 mg KOH/g, and the TONE series from Dow Chemical of Midland, Mich., such as TONE 0201, 0210, 0230 and 0241. In some non-limiting embodiments, the polycaprolactone polyol has a molecular weight ranging from about 500 to about 2000 grams per mole, or about 500 to about 1000 grams per mole.

Non-limiting examples of polycarbonate polyols include aliphatic polycarbonate diols, for example those based upon alkylene glycols, ether glycols, alicyclic glycols or mixtures thereof. In some non-limiting embodiments, the alkylene groups for preparing the polycarbonate polyol can comprise from 5 to 10 carbon atoms and can be straight chain, cycloalkylene or combinations thereof. Non-limiting examples of such alkylene groups include hexylene, octylene, decylene, cyclohexylene and cyclohexyldimethylene. Suitable polycarbonate polyols can be prepared, in non-limiting examples, by reacting a hydroxy terminated alkylene glycol with a dialkyl carbonate, such as methyl, ethyl, n-propyl or n-butyl carbonate, or diaryl carbonate, such as diphenyl or dinaphthyl carbonate, or by reacting of a hydroxy-terminated alkylene diol with phosgene or bischoloroformate, in a manner well-known to those skilled in the art. Non-limiting examples of suitable polycarbonate polyols include POLY-CD 210 hydroxyl-terminated 1000 MW poly(1,6-hexanediol)carbonate polyol commercially available from Arch Chemical.

Mixtures of any of the above polyols can be used.

In some non-limiting embodiments, the polyol can have a number average molecular weight of about 100 to about 10,000 grams/mole, or about 500 to about 5,000 grams/mole, or about 600 to about 3500 grams/mole.

In some non-limiting embodiments, the polyol can comprise about 10 to about 90 weight percent of the reactants used for preparing the urethane, or about 30 to about 70 weight percent of the reactants, or about 35 to about 65 weight percent of the reactants.

Recently, additional components have been included in traditional anaerobic adhesives to alter the physical properties of either the formulation or the reaction products thereof. For instance, one or more of maleimide components, thermal resistance-conferring co reactants, diluent components reactive at elevated temperature conditions, mono- or poly-hydroxyalkanes, polymeric plasticizers, and chelators (see U.S. Pat. No. 6,391,993, incorporated herein by reference) may be included to modify the physical property and/or cure profile of the formulation and/or the strength or temperature resistance of the cured adhesive.

When used, the maleimide, co reactant, reactive diluent, plasticizer, and/or mono- or poly-hydroxyalkanes, may be present in an amount within the range of about 1 percent to about 30 percent by weight, based on the total weight of the composition.

The inventive compositions may also include other conventional components, such as free radical initiators, free radical co-accelerators, and inhibitors of free radical generation, as well as metal catalysts.

A number of well-known initiators of free radical polymerization are typically incorporated into the inventive compositions including, without limitation, hydroperoxides, such as cumene hydroperoxide ("CHP"), para-menthane hydroperoxide, t-butyl hydroperoxide ("TBH") and t-butyl perbenzoate. Other peroxides include benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane and combinations thereof.

Such peroxide compounds are typically employed in the present invention in the range of from about 0.1 to about 10 percent by weight, based on the total weight of the composition, with about 1 to about 5 percent by weight being desirable.

As noted, conventional accelerators of free radical polymerization may also be used in conjunction with the inventive anaerobic cure accelerators, though in amounts less than that used in the past. Such accelerators are typically of the hydrazine variety (e.g., APH), as disclosed in U.S. Pat. No. 4,287,350 (Rich) and U.S. Pat. No. 4,321,349 (Rich). Maleic acid is usually added to APH-containing anaerobic cure systems. One benefit of the present invention is that the inventive anaerobic cure accelerators render the use of such acids unnecessary in preparing anaerobic adhesive compositions.

Co-accelerators of free radical polymerization may also be used in the compositions of the present invention including, without limitation, organic amides and imides, such as benzoic sulfimide (also known as saccharin) (See U.S. Pat. No. 4,321,349).

Stabilizers and inhibitors (such as phenols including hydroquinone and quinones) may also be employed to control and prevent premature peroxide decomposition and polymerization of the composition of the present invention, as well as chelating agents [such as the tetrasodium salt of ethylenediamine tetraacetic acid ("EDTA")] to trap trace amounts of metal contaminants therefrom. When used, chelating agents may ordinarily be present in the compositions in an amount from about 0.001 percent by weight to about 0.1 percent by weight, based on the total weight of the composition.

The inventive anaerobic cure accelerators may be used in amounts of about 0.1 to about 5 percent by weight, such as about 1 to about 2 percent by weight, based on the total weight of the composition. When used in combination with conventional accelerators (though at lower levels than such conventional accelerators), the inventive accelerators should be used in amounts of 0.01 to 5 percent by weight, such as 0.02 to 2 percent by weight, based on the total weight of the composition.

Metal catalyst solutions or pre-mixes thereof are used in amounts of about 0.03 to about 0.1 percent by weight.

Other additives such as thickeners, non-reactive plasticizers, fillers, toughening agents (such as elastomers and rubbers) and other well-known additives may be incorporated therein where the art-skilled believes it would be desirable to do so.

The present invention also provides methods of preparing and using the inventive anaerobic adhesive compositions, as well as reaction products of the compositions.

The compositions of the present invention may be prepared using conventional methods which are well known to those persons of skill in the art. For instance, the components of the inventive compositions may be mixed together in any convenient order consistent with the roles and functions the components are to perform in the compositions. Conventional mixing techniques using known apparatus may be employed.

The compositions of this invention may be applied to a variety of substrates to perform with the desired benefits and advantages described herein. For instance, appropriate substrates may be constructed from steel, brass, copper, aluminum, zinc, and other metals and alloys, ceramics and thermosets. The compositions of this invention demonstrate particularly good bond strength on steel, brass, copper and zinc. An appropriate primer for anaerobic curable compositions may be applied to a surface of the chosen substrate to enhance cure rate. Or, the inventive anaerobic cure accelerators may be applied to the surface of a substrate as a primer. See e.g. U.S. Pat. No. 5,811,473 (Ramos).

In addition, the invention provides a method of preparing an anaerobic curable composition, a step of which includes mixing together a (meth)acrylate component, an anaerobic cure inducing composition comprising an anaerobic cure accelerator compound of Formula (I) or a reaction product as discussed above.

The invention also provides a process for preparing a reaction product from the anaerobic curable composition of the present invention, the steps of which include applying the composition to a desired substrate surface and exposing the composition to an anaerobic environment for a time sufficient to cure the composition.

This invention also provides a method of using as a cure accelerator for anaerobic curable composition, compound of Formula (I) or a reaction product as discussed above.

And the present invention provides a method of using an anaerobic cure accelerator compound, including (I) mixing the anaerobic cure accelerator compound in an anaerobic curable composition or (II) applying onto a surface of a substrate the anaerobic cure accelerator compound and applying thereover an anaerobic curable composition. Of course, the present invention also provides a bond formed between mated substrates with the inventive composition.

In view of the above description of the present invention, it is clear that a wide range of practical opportunities are provided. The following examples are illustrative purposes only, and are not to be construed so as to limit in any way the teaching herein.

EXAMPLES

Synthesis of Phenylhydrazine-Glycerol Carbonate (PHGC) Reaction Products

An investigation was performed to evaluate phenylhydrazine-glycerol carbonate-isocyanate reaction products or resins as replacements for APH cure accelerator, for example, in anaerobic curable compositions, such as adhesives.

Phenylhydrazine-glycerol carbonate adducts were prepared in accordance with the synthetic scheme depicted below:

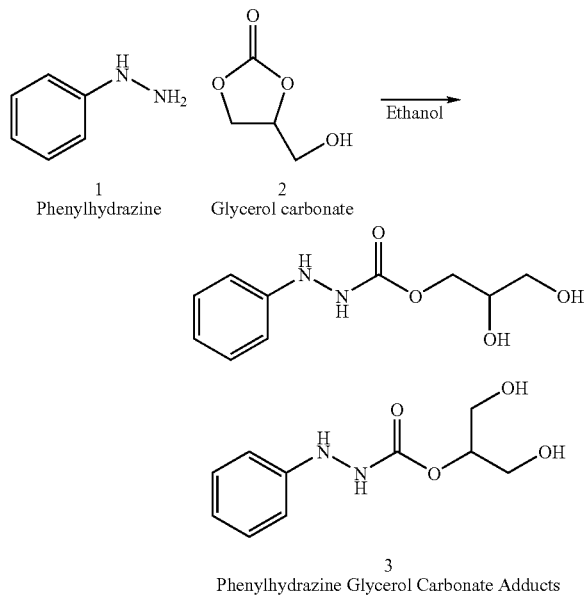

Phenylhydrazine Glycerol Carbonate Adducts

Phenylhydrazine and glycerol carbonate were reacted in the presence of ethanol in amounts and the manner described below to form PHGC reaction products (adducts) as shown in Table 1:

TABLE 1

| Reagents and Materials: | | | | |
|---|---|---|---|---|
| Reagent | Phenylhydrazine | Glycerol Carbonate | Ethanol | Adducts |
| Supplier | Aldrich | Ube Ind. | — | — |
| C.A.S. No. | 100-63-0 | 931-40-8 | 64-17-5 | — |
| Molecular Weight (g/mole) | 108.14 | 118.09 | 46.07 | 226.23 |
| % Active | 97 | est* 93.5% | — | — |
| Melting point (° C.) | 18-21 | — | — | — |
| Boiling point (° C.) | 238-241 | — | 78 | — |
| Density g/ml | 1.099 | — | 0.789 | — |
| | | | | Theoretical Yield |
| Amount (g) | 50.00 | 59.50 | 100 ml | 101.5 |
| mmols | 448.50 | 471.00 | | 448.50 |

*Estimated 93.5% based on Huntsmann MSDS.

Example A

To a 3 necked, 500 ml round-bottomed flask equipped with magnetic stirring, a reflux condenser, pressure equilibrated addition funnel, nitrogen purge and thermo-probe was added phenylhydrazine (liquid 1) (50.0 g, 448.5 mmol) followed by ethanol (50 ml). To this clear solution was added a solution of glycerol carbonate (liquid 2) (59.5 g, 471.0 mmol) and the solvent ethanol (50 ml). This was added over 30 minutes at room temperature (about 25° C.), whereby the mixture remained clear with a minimal exotherm. The mixture was warmed to 70° C. and allowed to stir overnight. The temperature was raised the following day to a gentle reflux of 78° C. After five days, an aliquot was analyzed by FT-IR. It appeared by IR that more progress was made. The reaction was ended.

The reaction mixture was concentrated in vacuo (about 60° C. and 100 Torr) to a pale amber oil. This oil was further concentrated in vacuo (about 60° C. and 10 Torr) to a pale amber viscous oil/solids (113.01 g; 111.3% of theoretical yield). It was believed that this sample still contained residual ethanol since the weight exceeded the calculated yield. The oil was placed in a refrigerator at a temperature of about 10° C.

It was observed that phenylhydrazine has limited solubility in water (~10% by weight) and the glycerol carbonate appeared very soluble in water. A small amount of the above reaction product (~10 g) was re-dissolved in ethyl acetate (100 ml) and washed with water (100 ml). The organic portion was separated and dried with anhydrous $MgSO_4$, gravity filtered and then concentrated in vacuo to an oil (5.1 grams, 51 weight % recovery). The oil was placed in a refrigerator at a temperature of about 10° C. The material was further dried in vacuo at about 100 mTorr and 50° C. to provide Sample A. The solid was analyzed by FT-IR, $^1$H NMR and $^{13}$C NMR. Proton Nuclear Magnetic Resonance analyses were performed using a Varian 300 MHz Gemini Spectrophotometer. Melting points were obtained on a TA Instrument 2920 Differential Scanning Calorimeter.

FIG. 1 provides the result of an FT-IR analysis of PHGC reaction product Sample A. The results clearly show that nearly all anhydride was consumed. $^1$H NMR: (DMSO-d6, 300 MHz) δ 9.0, 7.65, 7.15, 6.6, 5.2-3.35, 2.0. $^{13}$C NMR: (DMSO-d6, 75 MHz) δ 157.5, 150.0, 129.5, 119.5, 112.5, 74.0, 67.5, and 66.5.

Example B

Phenylhydrazine (50.0 g, 0.462 mol) was mixed with glycerol carbonate (54.6 g, 0.462 mol) at room temperature (about 25° C.). An exotherm to 35° C. was observed within about 5 minutes. FT-IR indicated C=O shift from 1762 cm$^{-1}$ to 1778 cm$^{-1}$ in about 10 minutes. Fifty ml of toluene was added and the mixture was stirred overnight with 20 g of activated acidic alumina. The filtered mixture was stripped for 2 hours at 75° C. and 0.3 mm Hg to yield 92 g of red, viscous syrup.

Example C

Synthesis of SPH-Glycidol Reaction Product

As an alternative to phenylhydrazine-glycerol carbonate, a SPH-glycidol reaction product can be used to prepare a resin of the present invention. (4-oxo-4-(2-phenylhydrazinyl)butanoic acid) ("SPH") and glycidol were reacted in the presence of acetonitrile in amounts and the manner described below to form a reaction product (adduct), which can be used as an anaerobic cure accelerator. The reaction product was prepared in accordance with the synthetic scheme depicted below from the reactants set forth in Table 2:

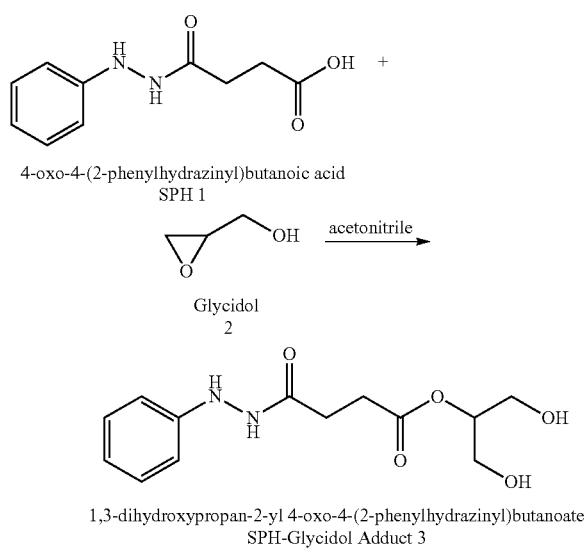

4-oxo-4-(2-phenylhydrazinyl)butanoic acid
SPH 1

Glycidol
2

1,3-dihydroxypropan-2-yl 4-oxo-4-(2-phenylhydrazinyl)butanoate
SPH-Glycidol Adduct 3

TABLE 2

Reagents and Materials:

| Reagent | SPH | Glycidol | Acetonitrile | Adduct |
|---|---|---|---|---|
| C.A.S. No. | x | 556-52-5 | 75-05-8 | x |
| Molecular Weight (g/mole) | 208.21 | 74.08 | 41.05 | 282.29 |
| % Active | x | 96 | 99 | x |
| Density g/ml | x | 1.12 @ 25° C. | 0.79 | x |
|  |  |  |  | Theoretical Yield |
| Amount (g) | 3.00 | 1.54 | 50 ml | 4.07 |
| mmols | 14.41 | 20.00 |  | 14.41* |

*97.8% of theoretical yield was obtained.

Figure 2:
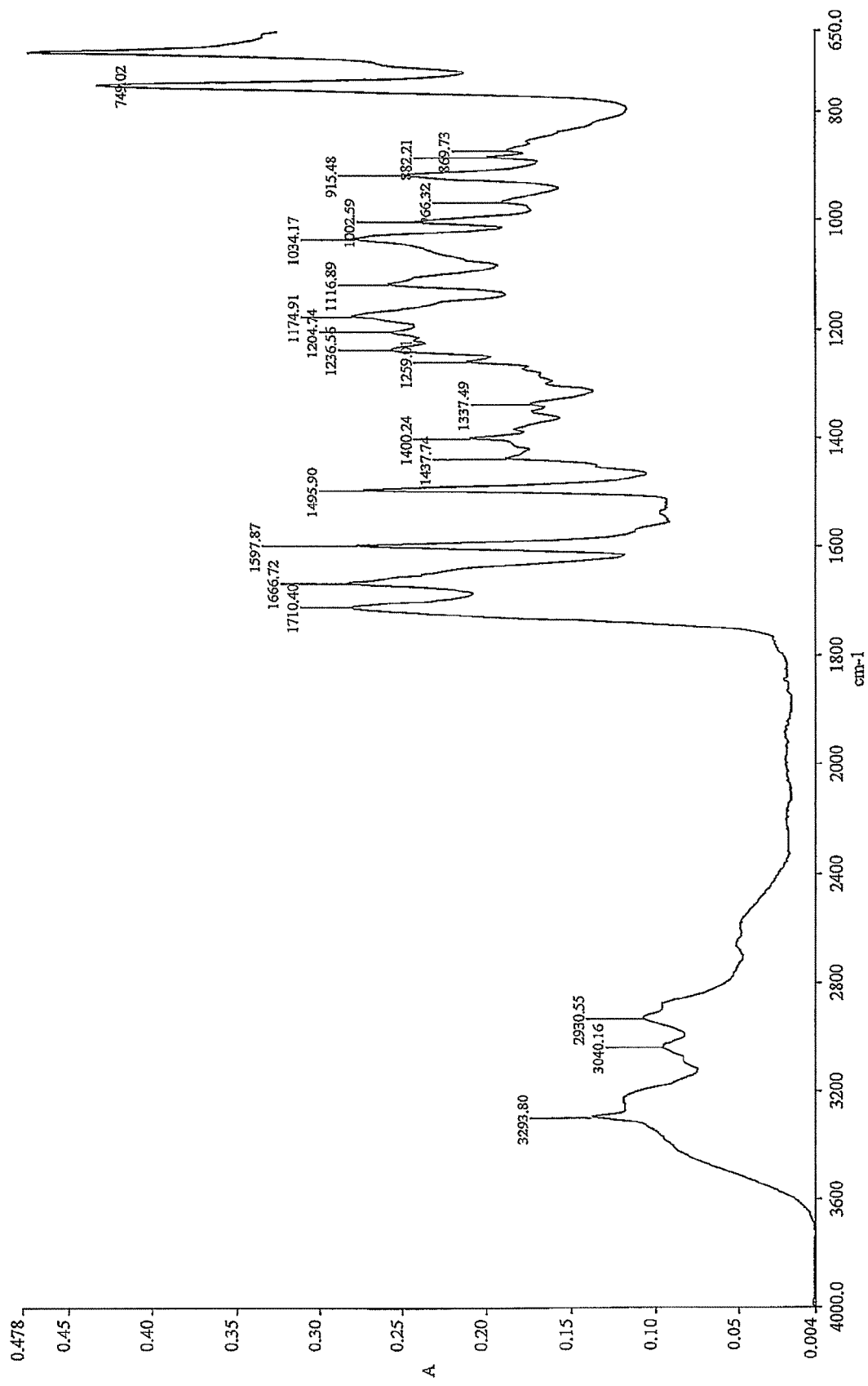
FIG. 2 depicts an IR spectra of an SPH-glycidol reaction product of Example C according to the present invention.

To a 3 neck 100 ml round bottom equipped with magnetic stirring, a reflux condenser, pressure equilibrated addition funnel, nitrogen purge and thermo-probe was added SPH (liquid 1) (3.00 g, 14.41 mmol), followed by the solvent acetonitrile (50 ml). The white suspension was warmed to 60° C., then the glycidol was added. The suspension clarified as it was stirred over the weekend at 60° C. An aliquot was taken and analyzed by Infrared ("IR") spectral analysis using a Perkin Elmer FT-IR to confirm structure. The clear pale amber liquid was concentrated in vacuo at 40° C. to a pale brown solid. The solid was further dried in vacuo at 50° C. The dried SPH-Glycidol Adduct was a light brown solid (3.98 g, 97.8% of theoretical yield). The solid was evaluated by $^1$H NMR, $^{13}$C NMR and FT-IR. The results of FT-IR analysis of the SPH-glycidol reaction product is shown in FIG. 2. $^1$H NMR: (DMSO-d6, 300 MHz) δ 9.95, 9.65, 7.1, 6.7, 5.1, 4.05, 3.9, 3.7, 3.4, 2.7, 2.6, 2.4. $^{13}$C NMR (DMSO-d6, 75 MHz) δ 175.0, 172.0, 150.0, 130.0, 119.0, 113.0, 77.0, 69.0, 64.0, 29.5, and 29.0.

Resin Preparation A

Phenylhydrazide-Carbonate Adduct Resin Preparation:

The following abbreviations have the following meanings as used herein:

Bi(Oct)$_3$ means bismuth 2-ethylhexanoate, 70% in 2-ethylhexanoic acid from King Industries.
BHT means butylated hydroxytoluene.
DBTDL means dibutyltin dilaurate.
IPDI means isophorone diisocyanate.
MDEA means N-methyldiethanolamine.
MeHQ means paramethoxyphenol or monomethyl ether hydroquinone.
MW means number average molecular weight.
TRIEGMA means triethylene glycol di-methacrylate.
TMXDI means m-tetramethylxylylene diisocyanate.

The following components were reacted as discussed below to form an accelerating resin according to the present invention:

| Component | Weight (g) | Moles | Equiv. Ratio | Weight % |
|---|---|---|---|---|
| IPDI | 72.58 | 0.327 | 2.000 | 25.81% |
| CAPA 2085 polycaprolactone polyol | 131.75 |  | 1.000 | 46.85% |
| 2-Hydroxyethyl Methacrylate | 23.54 | 0.163 | 0.500 | 8.37% |
| Phenylhydrazide-Carbonate Adduct | 12.37 | 0.082 | 0.500 | 4.40% |
| IRGANOX 1010 phenolic antioxidant[1] | 0.14 |  |  |  |
| MeHQ | 0.14 |  |  |  |
| DBTDL | 0.11 |  |  | 0.04% |
| Bi(Oct)$_3$ | 0.36 |  |  | 0.13% |
| TRIEGMA[2] | 40.21 |  |  | 14.30% |
| Theoretical Yield (g): | 281.20 |  |  |  |

[1]IRGANOX 1010 phenolic antioxidant commercially available from Ciba Specialty Chemicals.

The Phenylhydrazide-Carbonate Adduct was prepared as follows. To a three-necked, 500 ml round-bottomed flask equipped with magnetic stirring, a reflux condenser, pressure equilibrated addition funnel, nitrogen purge and thermo-probe was added glycerol carbonate (liquid 2) (70.81 g, 560.7 mmol) followed by ethanol (40 ml). To this clear solution was added a solution of phenylhydrazine (liquid 1) (50.0 g, 448.5 mmol) and the solvent ethanol (40 ml). This solution was added slowly over 30 minutes at room temperature (about 25° C.), whereby the mixture remained clear with a minimal exotherm. The mixture was warmed to 70° C. and allowed to stir overnight. The progress was monitored by Quantitative $^{13}$C NMR and FT-IR. After three days, the reaction was ended. The reaction mixture was concentrated in vacuo (about 60° C. and 100 Torr), to a dark oil. The oil was redissolved in ethyl acetate (125 ml) and then washed with 1N HCl (500 ml) and water (500 ml). The organic portion was treated with a portion of activated carbon (~20 g), and stirred overnight. The carbon was removed by filtration and the filtrate was concentrated in vacuo to an oil (PHGC #1).

To a three-necked, 500 ml round-bottomed flask equipped with magnetic stirring, a reflux condenser, pressure equilibrated addition funnel, nitrogen purge and thermo-probe was added glycerol carbonate (liquid 2) (119.0 g, 942.0 mmol) followed by 1,2-diethoxyethane (100 ml). To this clear solution was added a solution of phenylhydrazine (liquid 1) (100.0 g, 897.0 mmol) and the solvent 1,2-diethoxyethane (100 ml). This solution was added slowly over 30 minutes at room temperature (about 25° C.), whereby the mixture remained clear with a minimal exotherm. The mixture was warmed to 100° C. and allowed to stir overnight. Each morning, an aliquot was analyzed by Quantitative $^{13}$C NMR. The reaction was ended after the second day. To the cooled reaction mixture was added activated carbon (13 g). This was stirred for ~1 hour. The mixture was vacuum filtered through silica (200 g) in a glass-fritted funnel (coarse) (pre-wetted with 300 ml of 1,2-diethoxyethane). The filtrate was collected and then gravity filtered through fluted paper to remove any fine particles, before it was concentrated in vacuo near 50 Torr and 80° C. to an amber viscous liquid that became solid upon standing (34.7% of theoretical yield) (PHGC #2).

The crude PHGC #1 and crude PHGC #2 were combined and dissolved in a minimal amount of methanol, enough to dissolve all solids and make the oil more flowing. This organic was purified by flash chromatography through silica gel (Davisil Grade 633 Type 60A). The desired fractions were combined and concentrated in vacuo to provide a dark olive-colored oil, identified as the target. The oil was identified by $^1$H NMR, and particularly Quantitative $^{13}$C NMR. $^1$H NMR: (DMSO-d6, 300 MHz) δ 9.05, 9.0, 7.65, 7.10, 6.65, 5.25, 4.90-4.80, 4.50-4.40, 4.30, 4.0-3.90, 3.60 and 3.30. $^{13}$C NMR: (DMSO-d6, 75 MHz) δ 157.5, 150.0, 129.5, 119.5, 112.5, 74.0, 67.5, 66.0, 64.0, and 60.5.

CAPA 2085 polycaprolactone polyol, IPDI, TRIEGMA, IRGANOX 1010 phenolic antioxidant, MeHQ, and DBTDL were added to a reaction flask and stirred at 75° C. for 1 hour under dry air. HEMA was added and the mixture was stirred for 1 hour at 75° C. The reaction product was titrated for "B" stage NCO. The Phenyl-Hydrazide Carbonate Adduct and Bi(Oct)$_3$ were added and the mixture was stirred for 8 hours at 75° C. IR showed 0.04 wt % NCO. Yield: 268.4 g of a light yellow, very viscous resin.

Preparation of Anaerobic Curable Compositions A

Selected components were premixed prior to mixing with the remaining components of the anaerobic base composition, as follows:

| Premix A: | |
|---|---|
| Component | % by weight |
| Polyethylene glycol dimethacrylate | 95 |
| Phenolic Stabilizer | 5 |

The components of Premix A were mixed by conventional stirring at about 25° C.

| Premix B: | |
|---|---|
| Component | % by weight |
| Propylene glycol | 73.5 |
| Water (deionized) | 23 |
| Chelating agent | 3.5 | the components of Premix B were mixed by conventional stirring at about 25° C.

Premixes A and B were used to prepare the Anaerobic Curable Compositions A according to Table 3 as follows:

TABLE 3

| Material | Generic Description | A part | B part | C part | D part | E part | F part |
|---|---|---|---|---|---|---|---|
| Polyethylene glycol (PEG) dimethacrylate | Dimethacrylate Monomer | 57.36 | 57.36 | 57.36 | 50.81 | 43.11 | 27.71 |
| Premix A | Phenolic Stabilizer Premix | 0.20 | 0.20 | 0.20 | 0.20 | 0.20 | 0.20 |
| Premix B | Chelating Stabilizer Premix | 1.25 | 1.25 | 1.25 | 1.25 | 1.25 | 1.25 |
| Tetraethylene glycol di (2-ethylhexoate) | Plasticizer/Diluent | 28.74 | 28.56 | 28.89 | 27.74 | 27.74 | 27.74 |
| Polyvinyl acetate Beads | Viscosity Modifier | 5.00 | 5.00 | 5.00 | 5.00 | 5.00 | 5.00 |
| Polyethylene Powder | Viscosity Modifier | 3.00 | 3.00 | 3.00 | 3.00 | 3.00 | 3.00 |
| Aerosil R972 | Fumed Silica | 2.00 | 2.00 | 2.00 | 2.00 | 2.00 | 2.00 |
| Saccharin | Conventional Anaerobic Accelerator | 1.00 | 1.00 | 1.00 | 1.00 | 1.00 | 1.00 |
| Maleic acid | Maleic acid | 0.30 | 0.30 | 0.30 | 0.30 | 0.30 | 0.30 |
| Acetyl phenylhydrazine | Conventional Anaerobic Accelerator | 0.15 | 0.00 | 0.00 | 0.00 | 0.00 | 0.00 |
| Phenylhydrazide-Carbonate Adduct of Example A | Phenylhydrazide-Carbonate Adduct | 0.00 | 0.33 | 0.00 | 0.00 | 0.00 | 0.00 |
| Phenylhydrazide-Carbonate Adduct Resin | Phenylhydrazide-Carbonate Adduct Resin | 0.00 | 0.00 | 0.00 | 7.70 | 15.40 | 30.80 |
| Cumene hydroperoxide | Conventional Anaerobic Initiator | 1.00 | 1.00 | 1.00 | 1.00 | 1.00 | 1.00 |
| | | 100.00 | 100.00 | 100.00 | 100.00 | 100.00 | 100.00 |

The first seven components were mixed in the order listed in Table 3, except only 18.4 parts of tetraethylene glycol di (2-ethylhexoate) was used. The components were mixed using a stainless steel propeller-type mixer such that the components were dissolved. As the components were mixed, the thickener components slowly 'dissolved into' the formulation and thickened to form a mixture. Some components required additional mixing time (minimally overnight) to completely dissolve. The remainder of the tetraethylene glycol di (2-ethylhexoate) and the remaining components were added to the mixture and mixed as above. APH (150.18 g/mole) was included in Formulation A as an additional accelerator. The phenylhydrazine-glycerol carbonate adduct (MW=331.8 g/mole) of Example A was included in Formulation B as an additional accelerator. No accelerator was used in Formulation C (Control). The phenylhydrazine-glycerol carbonate adduct resin was included in Formulations D-F in different amounts as an additional accelerator.

Physical Property Evaluation

A phenylhydrazine-glycerol carbonate adduct cure system (Formulation B) and phenylhydrazine-glycerol carbonate adduct resins (Formulations D-F) of the present invention were compared with the formulations containing conventional cure component APH (Formulation A) and the Control Formulation C (no additional accelerator) by 82° C. accelerated stability and adhesion tests on steel nut/bolt specimens.

Shelf Life Stability

The 82° C. stability of the formulations was determined according to an evaluation in which the formulation is judged to have acceptable shelf stability if the adhesive formulation remains liquid for 3 hours or longer at 82° C. Three specimens of each of the above Formulations A-F were evaluated at 82° C. As shown in Table 4, the samples of Formulations B and D-E of the present invention generally provided acceptable stability at 82° C.

TABLE 4

| Formulation | 82° C. Stability in minutes |
|---|---|
| A | >120 |
|  | >120 |
|  | >120 |
| B | >120 |
|  | >120 |
|  | >120 |
| C | <90 |
|  | <90 |
|  | <90 |
| D | >120 |
|  | >120 |
|  | >120 |
| E | >120 |
|  | <120 |
|  | <120 |
| F | <90 |
|  | <90 |
|  | <90 |

Fixture Times

Breakloose/prevail adhesion testing was performed according to ASTM D5649. Breakloose torque is the initial torque required to decrease or eliminate the axial load in a seated assembly. Prevailing torque, after initial breakage of the bond, is measured at any point during 360° rotation of the nut. Prevailing torque is normally determined at 180° rotation of the nut. Steel 3/8×16 nuts and bolts were degreased with 1,1,1-trichloroethylene, adhesive was applied to the bolt, and the nut was screwed onto the bolt with a steel collar as a spacer.

Figure 3:
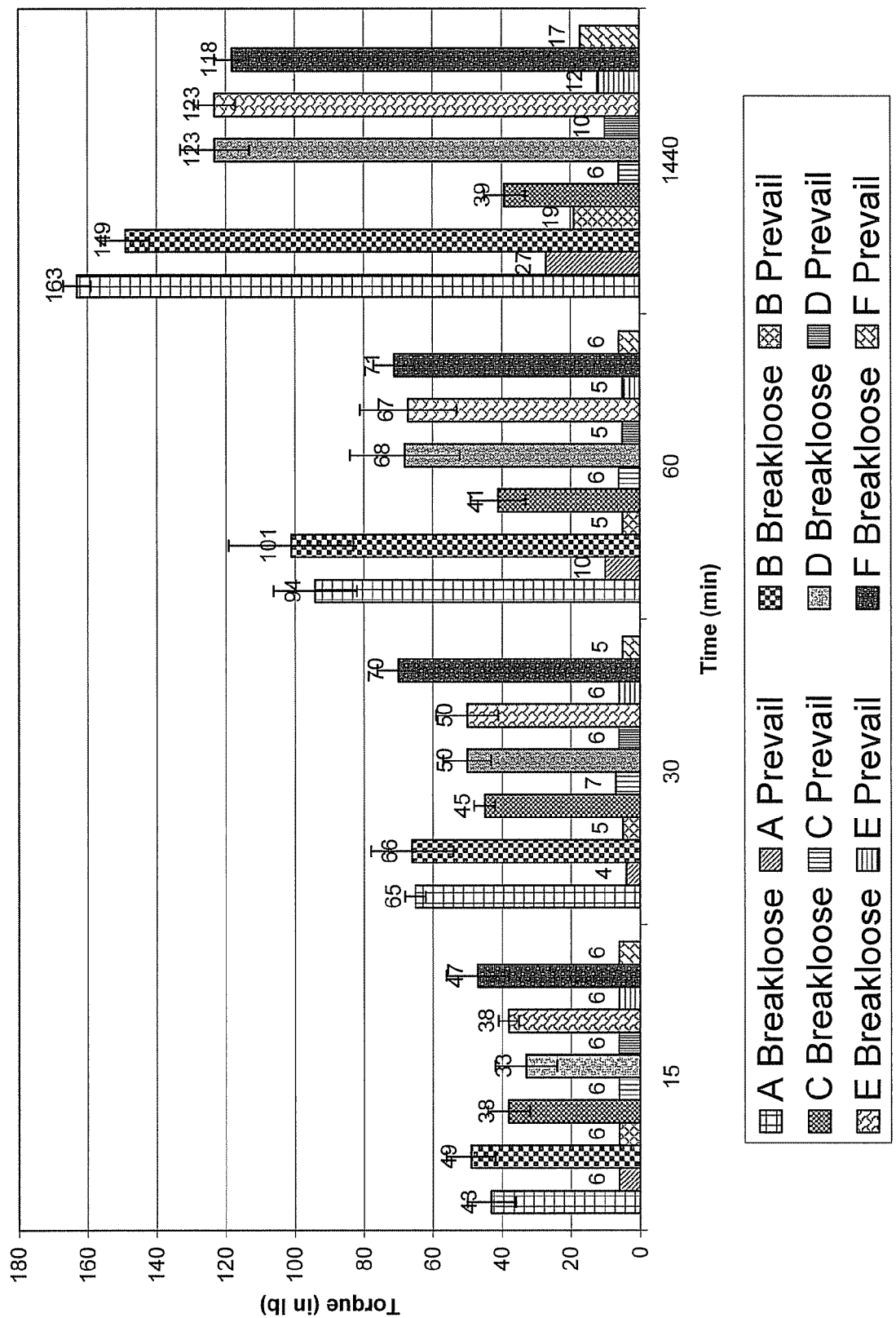
FIG. 3 depicts a bar chart of breakloose and prevailing torque on steel threaded fasteners of control adhesive compositions and adhesive compositions including a phenylhydrazine-glycerol carbonate reaction product according to the present invention.

Twenty nut and bolt specimens were assembled for each adhesive formulation tested. For the break/prevail adhesion tests, the specimens were maintained at ambient temperature for 15 minutes, 30 minutes, 1 hour and 24 hours after assembly (five specimens each). The break and prevail torque strengths (in-lb$_f$) were then recorded for five specimens of each adhesive formulation after 15 minutes, 30 minutes, one hour and after 24 hours at ambient temperature (25° C.) and 45-50% relative humidity, respectively. The torque strengths were measured using a calibrated automatic torque analyzer. The data for these evaluations is set forth below in Table 5 and FIG. 3.

This data indicates that Formulations D and E in accordance with this invention exhibited similar breakloose and prevail properties at room temperature compared to traditional anaerobic (meth)acrylate-based adhesives when applied and cured on the substrates.

TABLE 5

| | | Breakloose/180 Prevail (in lbs) | | | | | | |
|---|---|---|---|---|---|---|---|---|
| | | 15 minutes | | 30 minutes 30 | | 1 Hour | | 24 Hour 1440 |
| | | 15 | | 180 | | 60 | | 180 |
| Formula | | Break | 180 Prevail | Break | Prevail | Break | 180 Prevail | Break | Prevail |
| A | | 43 | 6 | 65 | 4 | 94 | 10 | 163 | 27 |
| | +/− | 7 | 0 | 3 | 1 | 12 | 17 | 4 | 7 |
| B | | 49 | 6 | 66 | 5 | 101 | 5 | 149 | 19 |
| | +/− | 7 | 0 | 12 | 1 | 18 | 1 | 7 | 6 |
| C | | 38 | 6 | 45 | 7 | 41 | 6 | 39 | 6 |
| | +/− | 6 | 0 | 3 | 0 | 8 | 1 | 6 | 0 |
| D | | 33 | 6 | 50 | 6 | 68 | 5 | 123 | 10 |
| | +/− | 9 | 0 | 7 | 0 | 16 | 3 | 10 | 6 |
| E | | 38 | 6 | 50 | 6 | 67 | 5 | 123 | 12 |
| | +/− | 3 | 0 | 9 | 1 | 14 | 3 | 6 | 3 |
| F | | 47 | 6 | 70 | 5 | 71 | 6 | 118 | 17 |
| | +/− | 9 | 0 | 6 | 0 | 6 | 5 | 5 | 4 |

What is claimed is:

1. A reaction product prepared from reactants comprising:
   (a) at least one compound selected from the group of compounds represented by structural Formula (I):

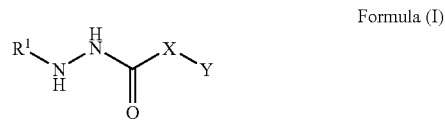

Formula (I)

wherein in Formula I:
R$^1$ is selected from the group consisting of aryl and heteroaryl;
X is selected from the group consisting of a direct bond, —O—, —S—, —NH—, alkylene, cycloalkylene, heterocyclylene, arylene, alkarylene, and heteroarylene;
Y is a substituted alkylene group comprising an alkylene backbone having at least two contiguous carbon atoms and which optionally can be interrupted by one or more —O—, —S—, or —NH— moieties,
provided that each —O—, —S—, or —NH— moiety of Y, if present, is not adjacent to an —O—, —S—, or —NH— of X,
wherein the alkylene group of Y has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl, and wherein at least two substituents of Y are each independently selected from the group consisting of —OH, —NH$_2$, and —SH, and provided that each of the —OH, —NH$_2$, -or —SH groups is not attached to the same carbon atom of Y or an —O—, —S—, or —NH— backbone moiety of Y; and (b) at least one isocyanate functional material.

2. The reaction product according to claim 1, wherein the reaction product comprises residual isocyanate functionality.

3. The reaction product according to claim 1, wherein the compound (a) is represented by structural Formula (A):

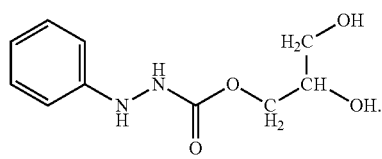

Formula (A)

4. The reaction product according to claim 1, wherein the compound (a) is represented by structural Formula (B):

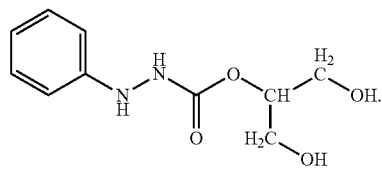

Formula (B)

5. The reaction product according to claim 1, wherein the at least one isocyanate functional material is selected from the group consisting of ethylene diisocyanate, trimethylene diisocyanate, 1,6-hexamethylene diisocyanate (HDI), tetramethylene diisocyanate, hexamethylene diisocyanate, octamethylene diisocyanate, nonamethylene diisocyanate, decamethylene diisocyanate, 1,6,11-undecanetriisocyanate, 1,3,6-hexamethylene triisocyanate, bis(isocyanatoethyl)-carbonate, bis(isocyanatoethyl)ether, trimethylhexane diisocyanate, trimethylhexamethylene diisocyanate (TMDI), 2,2'-dimethylpentane diisocyanate, 2,2,4-trimethylhexane diisocyanate, 2,4,4,-trimethylhexamethylene diisocyanate, 1,8-diisocyanato-4-(isocyanatomethyl)octane, 2,5,7-trimethyl- 1,8-diisocyanato-5-(isocyanatomethyl) octane, 2-isocyanatopropyl-2,6-diisocyanatohexanoate, lysinediisocyanate methyl ester, lysinetriisocyanate methyl ester, 4,4'-methylene-bis-(cyclohexyl isocyanate), 4,4'-isopropylidene-bis-(cyclohexyl isocyanate), 1,4-cyclohexyl diisocyanate (CHDI), 4,4'-dicyclohexylmethane diisocyanate, isophorone diisocyanate (IPDI), meta-tetramethylxylylene diisocyanate (TMXDI) and mixtures thereof.

6. The reaction product according to claim 1, wherein the reactants further comprise at least one functional material selected from the group consisting of hydroxy functional materials, amino functional materials, thio functional materials, and combinations and mixtures thereof.

7. The reaction product according to claim 1, wherein the hydroxy functional material is a hydroxy functional (meth)acrylate.

8. The reaction product according to claim 7, wherein the hydroxy functional (meth)acrylate is selected from the group consisting of hydroxymethyl (meth)acrylate, hydroxyethyl (meth)acrylate, hydroxypropyl (meth)acrylate, hydroxybutyl (meth)acrylate, hydroxypentyl (meth)acrylate, hydroxypropoxypropyl (meth)acrylate, diethylene glycol diacrylate, 1,6-hexanediol diacrylate, neopentyl glycol diacrylate, polyethylene glycol diacrylate, trimethylolpropane diacrylate and mixtures thereof.

9. The reaction product according to claim 6, wherein the amino functional material is an amino functional (meth)acrylate.

10. The reaction product according to claim 9, wherein the amino functional (meth)acrylate is a protected amino functional (meth)acrylate selected from the group consisting of 2-methylcarbamatoalkyl acrylate, ethylcarbamatoalkyl acrylate, propylcarbamatoalkyl acrylate, butylcarbamatoalkyl acrylate, isocyanatoethyl (meth)acrylate and mixtures thereof.

11. The reaction product according to claim 2, wherein the reaction product comprises residual isocyanate functionality and the reaction product is further reacted with at least one functional material selected from the group consisting of hydroxy functional materials, amino functional materials, thio functional materials and combinations and mixtures thereof.

12. A composition comprising the reaction product of claim 1.

13. The composition according to claim 12, further comprising at least one anaerobic curing component.

14. The composition according to claim 13, wherein the anaerobic curing component is a hydroperoxide selected from the group consisting of t-butyl hydroperoxide, p-methane hydroperoxide, cumene hydroperoxide (CHP), diisopropylbenzene hydroperoxide, and mixtures thereof.

15. The composition according to claim 12, further comprising at least one accelerator.

16. The composition according to claim 15, wherein the accelerator is selected from the group consisting of amines, amine oxides, sulfonamides, metal sources, acids, and mixtures thereof.

17. The composition according to claim 15, wherein the accelerator is selected from the group consisting of triazines, ethanolamine, diethanolamine, triethanolamine, N,N dimethyl aniline, benzene sulphanimide, cyclohexyl amine, triethyl amine, butyl amine, saccharin, N,N-diethyl-p-toluidine, N,N-dimethyl-o-toluidine, acetyl phenylhydrazine, maleic acid, and mixtures thereof.

18. The composition according to claim 12, further comprising at least one stabilizer.

19. The composition according to claim 18, wherein the stabilizer is selected from the group consisting of benzoquinone, naphthoquinone and anthraquinone, hydroquinone, methoxyhydroquinone, butylated hydroxy toluene, ethylene diamine tetraacetic acid or a salt thereof, and mixtures thereof.

20. A reaction product prepared from reactants comprising:

(a) at least one reaction product (A) prepared from reactants comprising:

(1) at least one compound selected from the group of compounds represented by structural Formula (II):

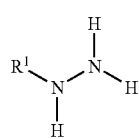

Formula (II)

wherein in Formula II:
$R^1$ is selected from the group consisting of aryl and heteroaryl; and (2) at least one compound selected from the group of compounds represented by structural Formula (III) and structural Formula (IV):

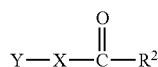

Formula (III)

wherein in Formula III:
X is selected from the group consisting of a direct bond, —O—, —S—, —NH—, alkylene, cycloalkylene, heterocyclylene, arylene, alkarylene, and heteroarylene;
Y is a substituted alkylene group comprising an alkylene backbone having at least two contiguous carbon atoms and which optionally can be interrupted by one or more —O—, —S—, or —NH— moieties,
provided that each —O—, —S—, or —NH— moiety of Y, if present, is not adjacent to an —O—, —S—, or —NH— of X,
wherein the alkylene group of Y has substituents which are independently selected from the group consisting of —OH, —NH₂, —SH, cycloalkyl, heterocyclyl, aryl, and heteroaryl, or two hydrogen atoms on the same carbon atom of Y are replaced by carbonyl, and
wherein at least two substituents of Y are each independently selected from the group consisting of —OH, —NH₂, and —SH, and
provided that each of the —OH, —NH₂, -or —SH groups is not attached to the same carbon atom of Y or an —O—, —S—, or —NH— backbone moiety of Y; and
$R^2$ is selected from the group consisting of —OR, NHR, alkyl, and arylalkyl,
wherein R is H, alkyl or arylalkyl; and

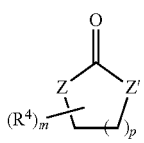

Formula (IV)

wherein in Formula IV:
Z and Z' are each independently selected from the group consisting of —O—, —S—, and
—NR³, wherein $R^3$ is H or alkyl;
m is at least 1;
each $R^4$ is independently selected from the group consisting of hydroxyalkyl, aminoalkyl, thioalkyl, hydroxyl substituted cycloalkyl, arylalkyl having at least one —OH, —NH₂, or —SH group, and heteroarylalkyl having at least one —OH, —NH₂, or —SH group, provided that there is no more than one $R^4$ substituent attached to a substitutable ring carbon atom; and p is 1 or 2; and (b) at least one isocyanate functional material.

21. The reaction product according to claim 20, wherein the compound of formula II is

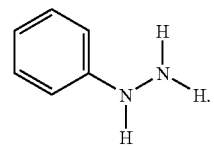

22. The reaction product according to claim 20, wherein the compound of Formula IV is

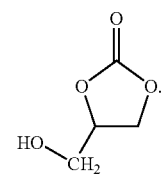

23. The reaction production according to claim 20, wherein the reaction product (A) comprises a composition represented by structural formula A:

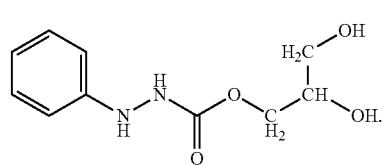

Formula (A)

24. The reaction production according to claim 20, wherein the reaction product (A) comprises a composition represented by structural formula B:

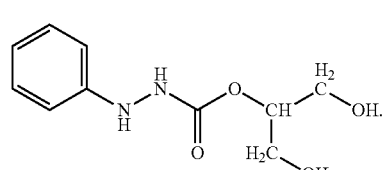

Formula (B)

25. A reaction product prepared from reactants comprising:
(a) at least one reaction product (B) prepared from reactants comprising:
(1) at least one compound selected from the group of compounds represented by structural Formula (V):

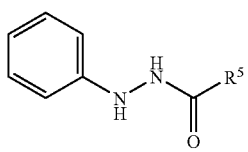

Formula (V)

wherein in Formula V:
$R^5$ is selected from the group consisting of hydroxyalkyl and carboxyalkyl; and
(2) at least one compound selected from the group of compounds represented by structural Formula (VI):

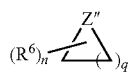

Formula (VI)

wherein in Formula VI:
Z" is selected from the group consisting of —O—, —S—, and —NH—;
q is 1 to 4;
$R^6$ is independently selected from the group consisting of hydroxyalkyl, aminoalkyl, and thioalkyl; and
n is at least 1; and
(b) at least one isocyanate functional material.

26. The reaction product according to claim 25, wherein the compound of Formula V is

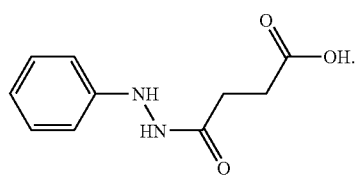

27. The reaction product according to claim 25, wherein the compound of Formula VI is

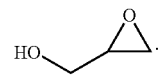

28. A method of making a reaction product prepared from reactants comprising reacting:
(a) at least one compound selected from the group of compounds represented by structural Formula (I):

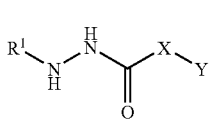

Formula (I)

wherein in Formula I:
$R^1$ is selected from the group consisting of aryl and heteroaryl;
X is selected from the group consisting of a direct bond, —O—, —S—, —NH—, alkylene, cycloalkylene, heterocyclylene, arylene, alkarylene, and heteroarylene;
Y is a substituted alkylene group comprising an alkylene backbone having at least two contiguous carbon atoms which optionally can be interrupted by an —O—, —S—, or —NH— moiety,
provided that the —O—, —S—, or —NH— of Y, if present, is not adjacent to another —O—, —S—, or —NH— group of X, wherein the alkylene group has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl, and
wherein at least two substituents are each independently selected from the group consisting of —OH, —NH$_2$, and —SH, and provided that each of the —OH, —NH$_2$, or —SH is not attached to the same carbon atom of Y or an —O—, —S—, or —NH— backbone moiety of Y; and
(b) at least one isocyanate functional material.

* * * * *

UNITED STATES PATENT AND TRADEMARK OFFICE
CERTIFICATE OF CORRECTION

PATENT NO. : 8,106,141 B2  
APPLICATION NO. : 12/116572  
DATED : January 31, 2012  
INVENTOR(S) : Anthony F. Jacobine et al.

It is certified that error appears in the above-identified patent and that said Letters Patent is hereby corrected as shown below:

Column 41, Line 4, Claim 1, delete "-or" and insert -- or --

Column 43, Line 44, Claim 20, delete "-or" and insert -- or --

Column 44, Line 34, Claim 23, delete "production" and insert -- product --

Column 44, Line 47, Claim 24, delete "production" and insert -- product --

Column 41, Lines 48-49, Claim 5, delete "2,5,7-trimethyl- 1" and insert -- 2,5,7-trimethyl-1 --

Column 41, Line 49, Claim 5, delete "(isocyanatomethyl) octane," and
insert -- (isocyanatomethyl)octane, --

Signed and Sealed this
Tenth Day of April, 2012

David J. Kappos
*Director of the United States Patent and Trademark Office*